United States Patent
Feurer et al.

(10) Patent No.: US 7,091,198 B1
(45) Date of Patent: Aug. 15, 2006

(54) 2,5-DISUBSTITUTED PYRIMIDINE DERIVATIVES

(75) Inventors: Achim Feurer, Wilhelmsfeld (DE); Joachim Luithle, Wülfrath (DE); Stephan-Nicholas Wirtz, Wuppertal (DE); Gerhard König, Arlington, MA (US); Johannes-Peter Stasch, Solingen (DE); Elke Stahl, Bergisch Gladbach (DE); Rudy Schreiber, Menlo Park, CA (US); Frank Wunder, Wuppertal (DE)

(73) Assignee: Bayer HealthCare AG, Leverkusen (DE)

( * ) Notice: Subject to any disclaimer, the term of this patent is extended or adjusted under 35 U.S.C. 154(b) by 0 days.

(21) Appl. No.: 10/521,538

(22) PCT Filed: Jul. 7, 2003

(86) PCT No.: PCT/EP03/07238

§ 371 (c)(1),
(2), (4) Date: Aug. 1, 2005

(87) PCT Pub. No.: WO2004/009589

PCT Pub. Date: Jan. 29, 2004

(30) Foreign Application Priority Data

Jul. 18, 2002 (DE) ................. 102 32 572

(51) Int. Cl.
*C07D 471/04* (2006.01)
*C07D 413/04* (2006.01)
*C07D 403/04* (2006.01)
*A61K 31/4162* (2006.01)
*C07D 231/38* (2006.01)

(52) U.S. Cl. ................ 514/211.09; 514/212.08; 514/221; 514/234.2; 514/234.6; 514/249; 514/256; 540/524; 540/543; 540/556; 544/71; 544/122; 544/328; 544/333

(58) Field of Classification Search ............... 540/524, 540/543, 556; 544/71, 122, 328, 333; 514/211.09, 514/212.08, 221, 234.2, 234.6, 256
See application file for complete search history.

(56) References Cited

FOREIGN PATENT DOCUMENTS

| DE | 19649460 | 5/1998 |
|---|---|---|
| DE | 19834045 | 2/2000 |
| DE | 19834047 | 2/2000 |
| DE | 19846514 | 4/2000 |

OTHER PUBLICATIONS

Vippagunta et al., Crystalline Solids, Advanced Drug Delivery Reviews 48:3-26, 2001.*
West, Solid Solutions, Solid State Chemistry and Its Applications, pp. 365, 1988.*
Carvajal et al., Molecular Mechanism of cGMP-mediated Smooth Muscle Relaxation, Journal of Cellular Physiology, 184:409-420, 2000.*
Yamashita et al., Mechanisms of Reduced Nitric Oxide/cGMP-mediated Vasorelaxation in Transgenic Mice Overexpressing Endothelial Nitric Oxide Synthase, Hypertension, 36:97-102, 2000.*
Fisker et al., PubMed Abstract (J Endocrinol Invest. 22(5 Suppl):89-93) 1999.*
Layzer, Degenerative Diseases of the Nervous System, Cecil Textbook of Medicine, 20th Edition, vol. 2, pp. 2050-2057, 1996.*
Damasio, Alzheimer's Disease and the related dementias, Cecil Textbook of Medicine, 20th Edition, vol. 2, pp. 1992-1996, 1996.*

* cited by examiner

*Primary Examiner*—Deepak Rao
(74) *Attorney, Agent, or Firm*—Susan M. Pellegrino

(57) ABSTRACT

The present invention relates to novel 2,5-disubstituted pyrimidine derivatives which stimulate soluble guanylate cyclase, to processes for the preparation thereof, and to the use thereof for producing medicaments, in particular medicaments for the treatment of central nervous system diseases.

8 Claims, No Drawings

2,5-DISUBSTITUTED PYRIMIDINE DERIVATIVES

This application is a 371 of PCT/EP2003/007238, filed Jul. 7, 2003.

The present invention relates to novel 2,5-disubstituted pyrimidine derivatives which stimulate soluble guanylate cyclase, to processes for the preparation thereof, and to the use thereof for producing medicaments, in particular medicaments for the treatment of disorders of the central nervous system.

One of the most important cellular signal transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyze the biosynthesis of cGMP from guanosine triposphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and contain at least one heme per heterodimer. The heme groups are part of the regulatory site and are of central importance for the mechanism of activation. NO is able to bind to the iron atom of heme and thus markedly increase the activity of the enzyme. Heme-free preparations cannot, by contrast, be stimulated by NO. CO is also able to attach to the central iron atom of heme, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed. In Alzheimers patients for example the NO-stimulated activity of soluble guanylate cyclase in the brain (cerebral cortex) is greatly reduced.

A reduced learning behavior can be observed in experimental animals on administration of dizocilpine, which leads to a reduced cGMP level (Yamada et al., Neuroscience 74 (1996), 365–374). This impairment can be abolished by injecting 8-Br-cGMP, a membrane-permeable form of cGMP. This is consistent with investigations showing that the cGMP level in the brain is increased after learning and memory tasks.

A possible treatment which is independent of NO and aims at influencing the cGMP signal pathway in organisms is a promising approach for stimulating soluble guanylate cyclase because of the high efficiency and few side effects which are to be expected.

Compounds, such as organic nitrates, whose effect is based on release of NO have to date been exclusively used for the therapeutic stimulation of soluble guanylate cyclase. NO is produced by bioconversion and activates soluble guanylate cyclase by binding to the central iron atom of heme. Besides the side effects, the development of tolerance is one of the crucial disadvantages of this mode of treatment.

Substances which directly stimulate soluble guanylate cyclase, i.e. without previous release of NO, have been described in recent years, such as, for example, 3-(5'-hydroxymethyl-2'-furyl)-1-benzylindazole (YC-1, Wu et al., Blood 84 (1994), 4226; Mülsch et al., Br. J. Pharmacol. 120 (1997), 681), fatty acids (Goldberg et al, J. Biol. Chem. 252 (1977), 1279), diphenyliodonium hexafluorophosphate (Pettibone et al., Eur. J. Pharmacol. 116 (1985), 307), isoliquiritigenin (Yu et al., Brit. J. Pharmacol. 114 (1995), 1587) and various substituted pyrazole derivatives (WO 98/16223).

In addition, WO 98/16507, WO 98/23619, WO 00/06567, WO 00/06568, WO 00/06569, WO 00/21954, WO 02/4229, WO 02/4300, WO 02/4301 and WO 02/4302 describe pyrazolopyridine derivatives as stimulators of soluble guanylate cyclase. Also described in these patent applications are pyrazolopyridines having various radicals. Compounds of this type have very high in vitro activity in relation to stimulating soluble guanylate cyclase. However, it has emerged that these compounds have some disadvantages in respect of their in vivo properties such as, for example, their behavior in the liver, their pharmacokinetic behavior, their dose-response relation or their metabolic pathway.

It was therefore the object of the present invention to provide further pyrimidine derivatives which act as stimulators of soluble guanylate cyclase but do not have the disadvantages, detailed above, of the compounds from the prior art. An additional advantage of novel medicaments for the treatment of disorders of the central nervous system (e.g. learning and memory impairments) would be an increased selectivity for peripheral cardiovascular effects. It was likewise intended to improve these (e.g. by better brain penetration) compared with the prior art.

This object is achieved according to the present invention by the compounds claimed in claim 1.

Specifically, the present invention relates to the compounds of the formula

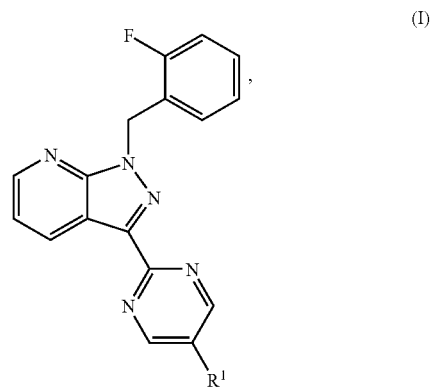

(I)

in which

R$^1$ is C$_6$–C$_{10}$-aryl or 5- to 10-membered heteroaryl which are optionally substituted by radicals selected from the group of halogen, cyano, C$_1$–C$_6$-alkoxy, C$_1$–C$_6$-alkoxycarbonyl, trifluoromethyl, 2,2,2-trifluoroethyl, trifluoromethoxy, C$_1$–C$_4$-alkyl and C$_3$–C$_8$-cycloalkyl, where C$_1$–C$_4$-alkyl is optionally substituted by hydroxy, or a group of the formula

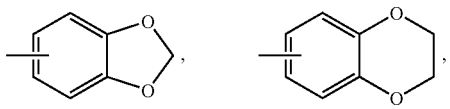

or 4- to 12-membered heterocyclyl which is bonded via a nitrogen atom and which is optionally substituted by radicals selected from the group of —NHR$^2$, halogen, $C_1$–$C_6$-alkoxycarbonyl, $C_1$–$C_6$-alkoxy, $C_1$–$C_6$-alkyl and oxo, where $C_1$–$C_6$-alkyl is optionally substituted by hydroxy, and R$^2$ is $C_1$–$C_4$-alkyl, or $C_4$–$C_8$-cycloalkyl which is substituted in the position adjacent to the point of attachment by oxo, and which is optionally substituted by $C_1$–$C_4$-alkyl, and the salts, solvates and/or solvates of the salts thereof.

Where asymmetric C atoms are present in R$^1$, the compounds of the invention can be in the form of enantiomers, diastereomers or mixtures thereof. These mixtures can be separated in a known manner into the stereoisomerically pure constituents.

Salts preferred for the purposes of the invention are physiologically acceptable salts of the compounds of the invention.

Physiologically acceptable salts of the compounds according to the invention may be acid addition salts of the compounds with mineral acids, carboxylic acids or sulfonic acids. Particularly preferred examples are salts with hydrochloric acid, hydrobromic acid, sulfuric acid, phosphoric acid, methanesulfonic acid, ethanesulfonic acid, p-toluenesulfonic acid, benzenesulfonic acid, naphthalenedisulfonic acid, acetic acid, propionic acid, lactic acid, tartaric acid, citric acid, fumaric acid, maleic acid or benzoic acid.

Physiologically acceptable salts may also be salts with usual bases, such as, for example, alkali metal salts (e.g. sodium or potassium salts), alkaline earth metal salts (e.g. calcium or magnesium salts) or ammonium salts derived from ammonia or organic amines such as, for example, diethylamine, triethylamine, ethyldiisopropylamine, procaine, dibenzylamine, N-methylmorpholine, dihydroabiethylamine, 1-ephenamine or methylpiperidine.

Solvates of the compounds of the invention are for the purposes of the invention stoichiometric compositions of the compounds or of their salts with solvents, e.g. water, ethanol.

For the purposes of the present invention, the substituents generally have the following meaning:

$C_1$–$C_6$-alkyl is a straight-chain or branched alkyl radical having 1 to 6 carbon atoms. Preference is given to a straight-chain or branched alkyl radical having 1 to 4, particularly preferably having 1 to 3, carbon atoms. Nonlimiting examples include methyl, ethyl, n-propyl, isopropyl, tert-butyl, n-pentyl and n-hexyl.

$C_1$–$C_6$-alkoxy is a straight-chain or branched alkoxy radical having 1 to 6 carbon atoms. Preference is given to a straight-chain or branched alkoxy radical having 1 to 4, particularly preferably having 1 to 3, carbon atoms. Nonlimiting examples include methoxy, ethoxy, n-propoxy, isopropoxy, tert-butoxy, n-pentoxy and n-hexoxy.

$C_1$–$C_6$-alkoxycarbonyl is a straight-chain or branched alkoxycarbonyl radical having 1 to 6 carbon atoms. Preference is given to a straight-chain or branched alkoxycarbonyl radical having 1 to 4, particularly preferably having 1 to 3, carbon atoms. Nonlimiting examples include methoxycarbonyl, ethoxycarbonyl, n-propoxycarbonyl, isopropoxycarbonyl and tert-butoxycarbonyl.

$C_6$–$C_{10}$-aryl is an aromatic radical having 6 to 10 carbon atoms. Nonlimiting examples include phenyl and naphthyl.

$C_3$–$C_8$-cycloalkyl is cyclopropyl, cyclopentyl, cyclobutyl, cyclohexyl, cycloheptyl or cyclooctyl. Nonlimiting examples include cyclopropyl, cyclopentyl and cyclohexyl.

Halogen is fluorine, chlorine, bromine and iodine. Fluorine, chlorine and bromine are preferred. Fluorine and chlorine are particularly preferred.

5- to 10-membered heteroaryl is an aromatic, mono- or bicyclic radical having 5 to 10 ring atoms and up to 5 heteroatoms from the series S, O and/or N. 5- to 6-membered heteroaryls having up to 4 heteroatoms are preferred. The heteroaryl radical may be bonded via a carbon atom or nitrogen atom. Nonlimiting examples include thienyl, furyl, pyrrolyl, thiazolyl, oxazolyl, imidazolyl, pyridyl, pyrimidyl, pyridazinyl, indolyl, indazolyl, isoxazyl, benzofuranyl, benzothiophenyl, quinolinyl, isoquinolinyl.

4- to 12-membered heterocyclyl is a mono- or polycyclic heterocyclic radical having 4 to 12 ring atoms and up to 3, preferably 2, heteroatoms or hetero groups from the series N, O, S, SO, SO$_2$. 4- to 8-membered heterocyclyl is preferred. Mono- or bicyclic heterocyclyl is preferred. N and O are preferred as heteroatoms. The heterocyclyl radicals may be saturated or partially unsaturated. Saturated heterocyclyl radicals are preferred. Nonlimiting examples include oxetan-3-yl, pyrrolidin-2-yl, pyrrolidin-3-yl, pyrrolinyl, tetrahydrofuranyl, tetrahydrothienyl, pyranyl, piperidinyl, thiopyranyl, morpholinyl, perhydroazepinyl, 9-oxa-3,7-diazabicyclo[3.3.1]nonanyl, 1-oxa-4,7-diazaspiro[5.4]decanyl, 10-oxa-4-azatricyclo[5.2.1.0$^{2,6}$]decanyl, 10-oxa-4-azatricyclo[5.2.1.0$^{2,6}$]decanyl, decahydropyrrolo[3,4-b]pyrrolizidinyl, 2,5-diazabicyclo[2.2.1]heptanyl, 8-oxa-3-azabicyclo[3.2.1]octanyl, octahydropyrrolo[3,4-d][1,3]oxazinyl.

Where the radicals in the compounds of the invention are substituted, the radicals may, unless otherwise specified, have one or more identical or different substituents. Substitution by up to three identical or different substituents is preferred. Substitution by one substituent is very particularly preferred.

Combinations of two or more of the preferred ranges mentioned above are very particularly preferred.

A further embodiment of the invention relates to compounds of the formula (I)

where

R$^1$ is phenyl or 5- to 6-membered heteroaryl which are optionally substituted by radicals selected from the group of fluorine, chlorine, cyano, $C_1$–$C_3$-alkoxycarbonyl, $C_1$–$C_3$-alkoxy, trifluoromethyl, 2,2,2-trifluoroethyl, trifluoromethoxy, $C_1$–$C_3$-alkyl and $C_3$–$C_5$-cycloalkyl, where $C_1$–$C_3$-alkyl is optionally substituted by hydroxy, or a group of the formula

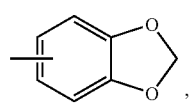

or
  4- to 12-membered heterocyclyl which is bonded via a nitrogen atom and which is optionally substituted by radicals selected from the group of —NHR$^2$, fluorine, chlorine, C$_1$–C$_3$-alkyl, C$_1$–C$_3$-alkoxycarbonyl, C$_1$–C$_3$-alkoxy and oxo, where C$_1$–C$_3$-alkyl is optionally substituted by hydroxy, and
  R$^2$ is C$_1$–C$_3$-alkyl,
or
  cyclohexyl which is substituted in the position adjacent to the point of attachment by oxo, and which is optionally substituted by C$_1$–C$_2$-alkyl,
and the salts, solvates and/or solvates of the salts thereof.

A further embodiment of the invention relates to compounds of the formula (I)
where
  R$^1$ is phenyl or pyridyl, pyrazolyl, isoxazolyl, which are optionally substituted by radicals selected from the group of fluorine, chlorine, cyano, methoxy, methoxycarbonyl, ethoxycarbonyl, trifluoromethyl, 2,2,2-trifluoroethyl, trifluoromethoxy, methyl, cyclopropyl or hydroxymethyl,
or a group of the formula

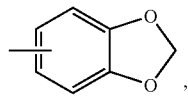

or
  4- to 12-membered heterocyclyl which is bonded via a nitrogen atom and which is optionally substituted by radicals selected from the group of —NHR$^2$, fluorine, chlorine, C$_1$–C$_3$-alkyl, methoxy, ethoxy, hydroxymethyl and oxo, and
  R$^2$ is methyl,
or
  cyclohexyl which is substituted in the position adjacent to the point of attachment by oxo, and which is optionally substituted by methyl,
and the salts, solvates and/or solvates of the salts thereof.

The invention further relates to processes for preparing the compounds of the invention, in which either
[A] compounds of the formula

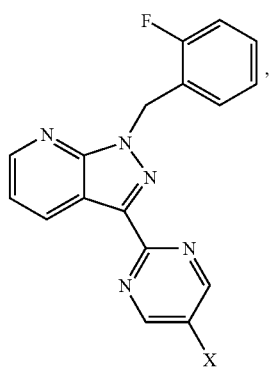

(II)

in which X is chlorine, bromine, iodine, preferably bromine, are reacted with a compound of the formula
(III),

R$^3$—NH—R$^4$    (III), in which

R$^3$, R$^4$ together with the nitrogen atom to which they are bonded, 4- to 12-membered heterocyclyl which is optionally substituted by radicals selected from the group of —NHR$^2$, halogen, C$_1$–C$_6$-alkoxycarbonyl, C$_1$–C$_6$-alkoxy, C$_1$–C$_6$-alkyl and oxo, where C$_1$–C$_6$-alkyl is optionally substituted by —OR$^5$, and R$^2$ has the meaning indicated above, R$^5$ is a hydroxy protective group, preferably tri-(C$_1$–C$_6$-alkyl)silyl, in an inert solvent in the presence of a base and of a transition metal catalyst to give compounds of the formula

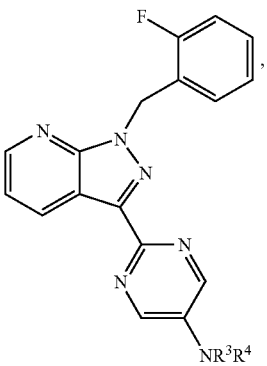

(IV)

or
[B] compounds of the formula (II) are reacted with a compound of the formula

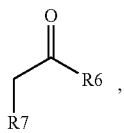

(V)

in which
  R$^6$ is cycloalkyl, R$^7$ is hydrogen or R$^6$ and R$^7$ together with the CH$_2$CO group to which they are bonded are cycloalkyl which may be substituted by C$_1$–C$_6$-alkyl radicals, in an inert solvent in the presence of a base and of a transition metal catalyst to give compounds of the formula

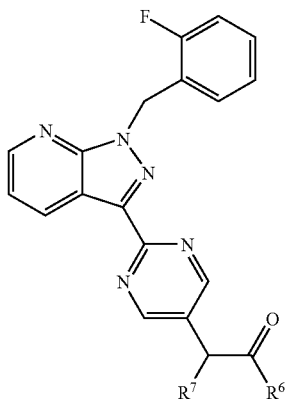

or

[C] compounds of the formula (II) are reacted with a compound of the formula

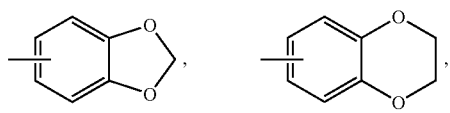

in which

A is —B(OR$^9$)$_2$ or —Sn(C$_1$–C$_6$-alkyl)$_3$, where
R$^9$ is hydrogen, C$_1$–C$_6$-alkyl or two radicals together form a —CH$_2$CH$_2$— or —(CH$_3$)$_2$C—C(CH$_3$)$_2$— bridge, and
R$^8$ is C$_6$–C$_{10}$-aryl or 5- to 10-membered heteroaryl which are optionally substituted by radicals selected from the group of halogen, cyano, C$_1$–C$_6$-alkoxy, C$_1$–C$_6$-alkoxycarbonyl, trifluoromethyl, 2,2,2-trifluoroethyl, trifluoromethoxy, C$_1$–C$_4$-alkyl and C$_3$–C$_8$-cycloalkyl, where C$_1$–C$_4$-alkyl is optionally substituted by hydroxyl, or a group of the formula in an inert solvent in the presence of a base and of a transition metal catalyst to give compounds of the formula

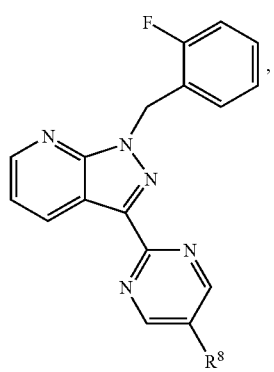

and the resulting compounds of the formula (I), (IV), (VI) and (VIII) are reacted where appropriate with the appropriate (i) solvents and/or (ii) bases or acids to give the solvates, salts or solvates of the salts thereof.

Preference is given to carrying out processes [A] and [B] of the invention in a temperature range from 20 to 100° C. and process [C] of the invention from 20 to 150° C. under atmospheric pressure.

Examples of inert solvents are ethers such as dioxane, tetrahydrofuran or 1,2-dimethoxyethane, hydrocarbons such as benzene, xylene or toluene, nitroaromatics such as nitrobenzene, optionally N-alkylated carboxamides such as dimethylformamide, dimethylacetamide, alkyl sulfoxides such as dimethyl sulfoxide or lactams such as N-methylpyrrolidone. Solvents from the series dimethylformamide, 1,2-dimethoxyethane, toluene and dioxane are preferred.

Examples of bases are alkali metal alcoholates such as, for example, sodium or potassium tert-butoxide or alkali metal carbonates such as cesium carbonate, sodium or potassium carbonate or alkali metal hydrides such as sodium or potassium hydride.

Transition metal catalysts may preferably be palladium(0) or palladium(II) compounds which can be employed preformed, such as, for example, bis(diphenyl-phosphaneferrocenyl)palladium(II) chloride, dichlorobis(triphenylphosphine)-palladium or be generated in situ from a suitable palladium source such as, for example, bis(dibenzylideneacetone)palladium(0) or tetrakistriphenylphosphine-palladium(0) and a suitable phosphine ligand. It is particularly preferred to employ 2,2'-bis(diphenylphosphino)-1,1'-binaphthalene (BINAP) as phosphine ligand.

The transition metal-catalyzed reactions can be carried out in analogy to processes known from the literature, e.g. reaction with alkynes; cf. N. Krause et al., *J. Org. Chem.* 1998, 63, 8551; with ketones, aromatics and alkenes; cf., for example, A. Suzuki, *Acc. Chem. Res.* 1982, 15, 178ff; Miyaura et al. *J. Am. Chem. Soc.* 1989, 111, 314; J. K. Stille, *Angew. Chem.* 1986, 98, 504 and with substituted amines: cf. S. L. Buchwald et al., *J. Organomet. Chem.* 1999, 576, 125ff. (see also J. Tsuji, Palladium Reagents and Catalysts, Wiley, New York, 1995).

The process of the invention can be illustrated by the following synthesis scheme.

Synthesis scheme:
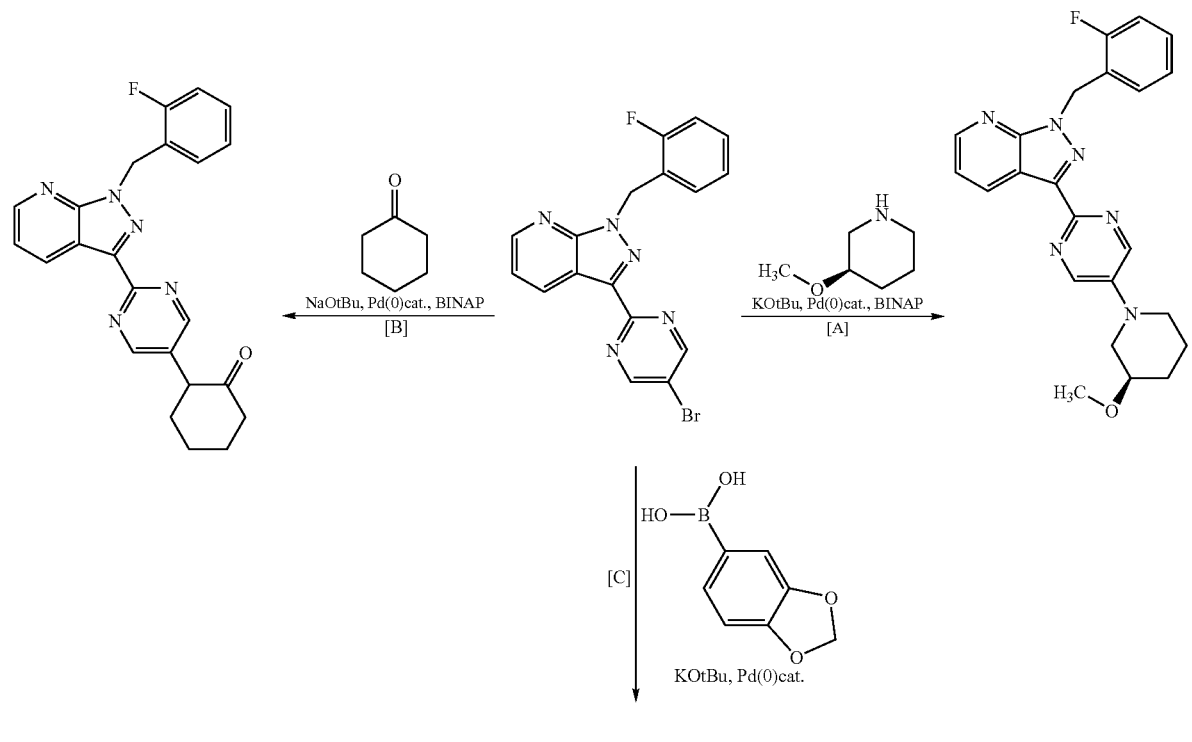
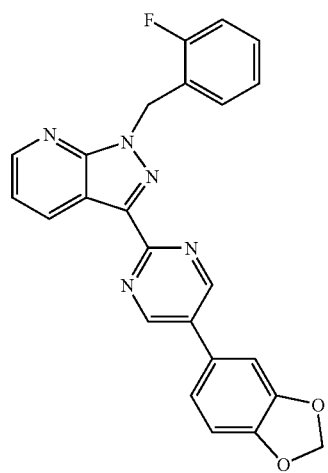

Functional groups can, where appropriate, be protected with suitable protective groups which can subsequently be eliminated again (cf., for example, T. W. Greene, P. Wuts, "Protective Groups in Organic Synthesis", 2nd edition, Wiley; New York, 1991).

The compounds of the formulae (IV), (VI) and (VII) can be converted by deprotection of functional groups and where appropriate a subsequent derivatization by known processes for alkylation, oxidation, reduction, etherification into the compounds of the formula (I) of the invention, which are reacted where appropriate with the appropriate (i) solvents and/or (ii) bases or acids to give the solvates, salts or solvates of the salts thereof. This is to be illustrated by the following synthesis scheme based on an example (deprotection, alkylation).

Synthesis scheme:

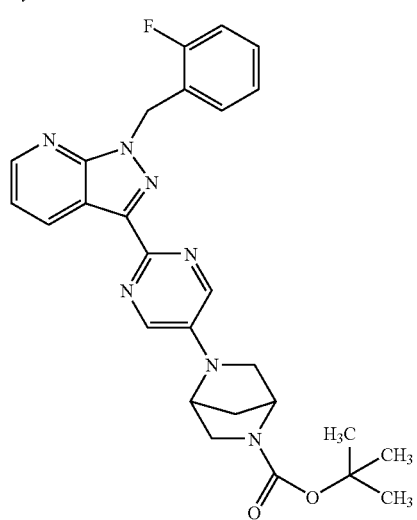

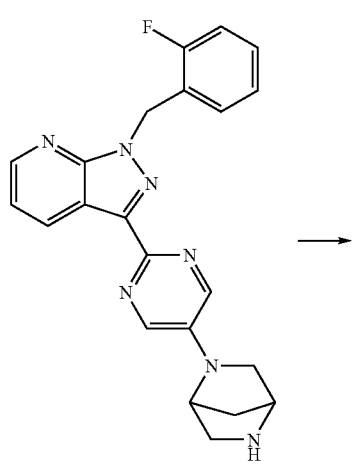

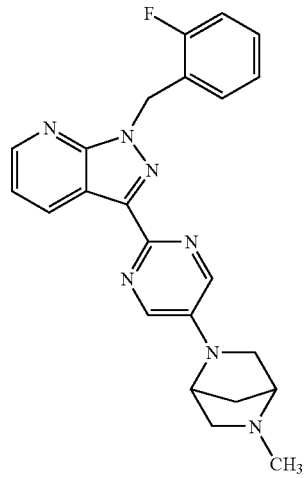

Compounds of the formula (II) can be prepared by reacting compound of the formula

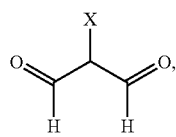

(IX)

in which X has the meaning indicated above, with a compound of the formula

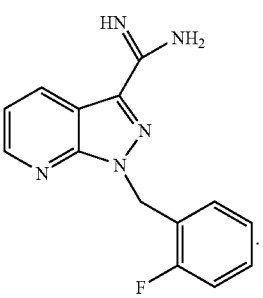

(X)

The compounds of the formula (III), (V), (VII) and (IX) are commercially available, known or can be prepared by known processes.

The compound of the formula (X) is disclosed in WO 00/06569.

The compounds of the invention show a valuable range of pharmacological effects which could not have been predicted.

The compounds of the invention increase the cGMP levels in neurons and thus represent active ingredients for controlling central nervous system diseases characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic cranial cerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, multiple sclerosis, thalamic degeneration, Creutzfeld-Jacob dementia, HIV dementia, schizophrenia with dementia or Korsakoff's psychosis.

The compounds of the invention also lead to vasorelaxation, platelet aggregation inhibition and to a reduction in blood pressure, and to an increase in the coronary blood flow. These effects are mediated by direct stimulation of soluble guanylate cyclase and an intracellular cGMP increase. In addition, the compounds of the invention may enhance the effect of substances which increase the cGMP level, such as, for example, EDRF (endothelium derived relaxing factor), NO donors, protoporphyrin IX, arachidonic acid or phenylhydrazine derivatives.

They can therefore be employed in medicaments for the treatment of cardiovascular disorders such as, for example, for the treatment of high blood pressure and heart failure, stable and unstable angina pectoris, peripheral and cardiac vascular disorders, of arrhythmias, for the treatment of thromboembolic disorders and ischemias such as myocardial infarction, stroke, transistorily and ischemic attacks, disturbances of peripheral blood flow, prevention of restenoses as after thrombolysis therapies by use in stents for example, percutaneously transluminal angioplasties (PTAs), percutaneously transluminal coronary angioplasties (PT-CAs), bypass operations and for the treatment of arteriosclerosis, asthmatic disorders, osteoporosis, gastroparesis, glaucoma and diseases of the urogenital system such as, for example, incontinence, prostate hypertrophy, erectile dysfunction and female sexual dysfunction.

They are also suitable for the treatment of central nervous system disorders such as states of anxiety, tension and depression, CNS-related sexual dysfunctions and sleep disturbances, and for controlling pathological disturbances of the intake of food, stimulants and addictive substances.

The compounds of the invention are additionally suitable for controlling cerebral blood flow and may represent effective agents for controlling migraine.

They are also suitable for the prophylaxis and control of the sequelae of cerebral infarctions such as stroke, cerebral ischemias and craniocerebral trauma. The compounds of the invention can likewise be employed for controlling states of pain.

In addition, the compounds of the invention have an anti-inflammatory effect.

Furthermore, the invention encompasses the combination of the compounds of the invention with organic nitrates and NO donors.

Organic nitrates and NO donors for the purposes of the invention are generally substances which release NO or NO precursors. Preference is given to sodium nitroprusside, nitroglycerine, isosorbide dinitrate, isosorbide mononitrate, molsidomine and SIN-1.

In addition, the invention encompasses the combination with compounds which inhibit breakdown of cyclic guanosine monophosphate (cGMP). These are in particular inhibitors of phosphodiesterases 1, 2 and 5; nomenclature of Beavo and Reifsnyder (1990), TiPS 11 pp. 150 to 155. These inhibitors potentiate the effect of the compound of the invention, and the desired pharmacological effect is increased.

The in vitro effect of the compounds of the invention can be shown in the following assays:

Increase of cGMP in Primary Cortical Neurons

Rat embryos (embryonic day 17–19) are decapitated, and the cerebrum is removed and incubated with 5 ml of papain solution and 250 µl of DNAse (papain kit from Cell-System) at 37° C. for 30 min, homogenized using a Pasteur pipette and centrifuged at 1200 rpm for 5 min. The supernatant is removed, the cell pellet resuspended (in 2.7 ml of EBSS [Earl's balanced salt solution], 300 µl of ovomucoid/albumin (conc.) solution, 150 µl of DNAse; papain kit from Cell-System), layered over 5 ml of ovomucoid/albumin solution and centrifuged at 700 rpm for 6 min. The supernatant is removed, the cells are resuspended in cultivation medium (Gibco neurobasal medium, B27 Supplement 50×1 ml/100 ml, 2 mM L-glutamine), counted (approx. 150 000 cells/well) and plated out on poly-D-lysine-coated 96-well plates (Costar) with 200 µl/well. After 6–7 days at 37° C. (5% $CO_2$), the neurons are freed of culture medium and washed once with assay buffer (154 mM NaCl, 5.6 mM KCl, 2.3 mM $CaCl_2.2H_2O$, 1 mM $MgCl_2$, 5.6 mM glucose, 8.6 mM HEPES (4-(2-hydroxyethyl)piperazine-1-ethanesulfonic acid), pH=7.4). 100 µl/well test substance are dissolved in assay buffer and then 100 µl/well IBMX (3-isobutyl-1-methylxanthine; dissolved in 50 mM ethanol, diluted with assay buffer to a final concentration of 100 µM) are added. After incubation at 37° C. for 20 min, the assay buffer is replaced by 200 µl/well of lysis buffer (cGMP EIA RPN 226 from Amersham Pharmacia Biotech), and the cGMP content of the lystates is determined using an EIA assay kit.

The concentrations indicated in Table 1 lead to a statistically significant increase in cGMP (triplicate determination; more than 2-fold increase compared with the control)

TABLE 1

| Example | µM |
|---------|------|
| 3 | 0.90 |
| 6 | 0.27 |
| 10 | 1.2 |
| 11 | 0.30 |
| 13 | 0.27 |
| 19 | 0.27 |
| 20 | 0.27 |
| 27 | 0.90 |
| 36 | 0.27 |
| 38 | 0.27 |

Vasorelaxant Effect In Vitro

Rabbits are stunned by a blow to the back of the neck and are exsanguinated. The aorta is removed, freed of adherent tissue, divided into rings 1.5 mm wide and put singly under tension in 5 ml organ baths containing carbogen-gassed Krebs-Henseleit solution at 37° C. with the following composition (mM): NaCl: 119; KCl: 4.8; $CaCl_2×2\ H_2O$: 1; $MgSO_4×7H_2O$: 1.4; $KH_2PO_4$: 1.2; $NaHCO_3$: 25; glucose: 10. The force of contraction is detected with Statham UC2 cells, amplified and digitized via A/D converters (DAS-1802 HC, Keithley Instruments Munich) and recorded in parallel on chart recorders. A contraction is generated by adding phenylephrine to the bath cumulatively in increasing concentration. After several control cycles, the substance to be investigated (dissolved in 5 μl of DMSO) is investigated in each further run in increasing dosage in each case, and the height of the contraction is compared with the height of the contraction reached in the last control cycle (control value). The concentration necessary to reduce the height of the control value by 50% ($IC_{50}$) is calculated from this.

Determination of the Liver Clearance In Vitro

Rats are anesthetized, heparinized, and the liver is perfused in situ via the portal vein. Primary rat hepatocytes are then obtained ex vivo from the liver using collagenase solution. $2.10^6$ hepatocytes per ml were incubated at 37° C. with the same concentration in each case of the compound to be investigated. The decrease of the substrate to be investigated over time was determined bioanalytically (HPLC/UV, HPLC/fluorescence or LC/MSMS) at 5 points in time in each case in the period from 0–15 min after the start of incubation. From this, the clearance was calculated by means of the cell count and liver weight.

Determination of the Plasma Clearance In Vivo

The substance to be investigated is administered as a solution intravenously to rats via the tail vein. At fixed points in time, blood is taken from the rats, heparinized and plasma is obtained therefrom by conventional measures. The substance is quantified bioanalytically in the plasma. The pharmacokinetic parameters are calculated from the plasma concentration-time courses determined in this way by means of conventional non-compartmental methods used for this purpose.

The suitability of the compounds of the invention for the treatment of disorders of perception, concentration, learning and/or memory can be shown for example in the following animal model:

Determination of the Learning and Memory in the Social Recognition Test

Adult Wistar rats (Winkelmann, Borchen; 4–5 months) and 4–5-week old pups are accustomed to their new environment for one week, with 3 animals being housed in each cage (Makrolon type IV) in a 12 h day-night rhythm (light on at 06:00) with water and food ad libitum. Usually, 4 groups of 10 animals (1 vehicle control group, 3 substance-treated groups) are tested. Firstly, all animals undergo a habituation run as in trial 1 but without substance or vehicle administration. The test substances are administered directly after trial 1. The social memory is measured in trial 2 after 24 h.

Trial 1: 30 min before testing, the adult rats are housed singly in cages (Makrolon type IV). 4 min before testing, a box consisting of two aluminum side walls, an aluminum back wall and a Plexiglas front (63×4 1×40 cm) is fitted over the cage, and the lid of the cage is removed. A pup is put with the adult rats in the cage, and the social interaction (e.g. sniffing) is timed for 2 min with a stopclock. The animals are then returned to their cage.

Trial 2: The test is repeated with the same animals after 24 h in analogy to trial 1. The difference between the social interaction time in trial 1 and trial 2 is taken as a measure of the social memory.

The compounds of the invention are suitable for use as medicaments for humans and animals.

The present invention includes pharmaceutical preparations which, besides inert, nontoxic, pharmaceutically suitable excipients and carriers, comprise one or more compounds of the invention, or which consist of one or more compounds of the invention, and processes for producing these preparations.

The compounds of the invention are to be present in these preparations in a concentration of from 0.1 to 99.5% by weight, preferably from 0.5 to 95% by weight, of the complete mixture.

The pharmaceutical preparations may, apart from the compounds of the invention, also comprise other active pharmaceutical ingredients.

The pharmaceutical preparations mentioned above can be produced in a conventional way by known methods, for example with the excipient(s) or carrier(s).

The novel active ingredients can be converted in a known manner into the usual formulations such as tablets, coated tablets, pills, granules, aerosols, syrups, emulsions, suspensions and solutions, using inert, nontoxic, pharmaceutically suitable carriers or solvent. In these cases, the therapeutically effective compound is to be present in each case in a concentration of about 0.5 to 90% by weight of the complete mixture, i.e. in amounts which are sufficient to achieve the indicated dosage range.

The formulations can be produced for example by diluting the active ingredients with solvents and/or carriers, where appropriate using emulsifiers and/or dispersants, it being possible for example in the case where water is used as diluent where appropriate to use organic solvents as auxiliary solvents.

Administration can take place in a conventional way, preferably orally, transdermally or parenterally, in particular perlingually or intravenously. However, it can also take place by inhalation through the mouth or nose, for example with the aid of a spray, or topically via the skin.

It has generally proved to be advantageous to administer amounts of about 0.001 to 10 mg/kg, on oral administration preferably about 0.005 to 3 mg/kg, of body weight achieve effective results.

It may nevertheless be necessary where appropriate to deviate from the stated amounts, in particular as a function of the body weight or the nature of the administration route, the individual response to the medicament, the nature of its formulation and the time or interval over which administration takes place. Thus, it may be sufficient in some cases to make do with less than the aforementioned minimum amount, where in other cases the stated upper limit must be exceeded. If larger amounts are administered, it may be advisable to divide these into a plurality of single doses over the day.

Abbreviations:

| | |
|---|---|
| ACN | acetonitrile |
| CI | chemical ionization (in MS) |
| DCM | dichloromethane |
| DME | 1,2-dimethoxyethane |
| DMF | N,N-dimethylformamide |
| DMSO | dimethyl sulfoxide |
| ESI | electrospray ionization (in MS) |
| GC | gas chromatography |
| HPLC | high pressure, high performance liquid chromatography |
| LC-MS | liquid chromatography-mass spectroscopy |
| m.p. | melting point |
| MS | mass spectroscopy |
| NMR | nuclear magnetic resonance spectroscopy |
| rac-BiNAP | rac-2,2-bis(diphenylphosphino)-1,1-dinaphthyl |
| $R_f$ | retention index (in TLC) |
| RT | room temperature, 20° C. |

| | |
|---|---|
| $R_t$ | retention time (in HPLC) |
| TFA | trifluoroacetic acid |
| THF | tetrahydrofuran |

Analytical Methods:

HPLC

Instrument: HP 1100 with DAD detection; column: Kromasil RP-18, 60 mm×2 mm, 3.5 μm; eluent: A=5 ml perchloric acid/l H₂O, B=ACN; gradient: 0 min 2% B, 0.5 min 2% B, 4.5 min 90% B, 6.5 min 90% B; flow rate: 0.75 ml/min; temp.: 30° C.; UV detection: 210 nm.

Preparative HPLC

Column: YMC GEL ODS-AQS-11 μm, 250 mm×30 mm; eluent: A=H₂O, B=ACN; gradient: 0 min 10% B, 10 min 10% B, 35 min 100% B, 45 min 100% B; flow rate: 33 ml/min; temp.: about 22° C.; UV detection: 254 nm.

LC/MS

Method A:

Instrument: Finnigan MAT 900S, TSP: P4000, AS3000, UV3000HR; column: Symmetry C 18, 150 mm×2.1 mm, 5.0 μm; eluent C: water, eluent B: water+0.3 g of 35% hydrochloric acid, eluent A: ACN; gradient: 0 min 2% A→2.5 min 95% A→5 min 95% A; oven: 70° C.; flow rate: 1.2 ml/min; UV detection: 210 nm.

Method B:

Instrument: Finnigan MAT 900S, TSP: P4000, AS3000, UV3000HR; column: Symmetry C 18, 150 mm×2.1 mm, 5.0 μm; eluent A: acetonitrile, eluent B: water+0.6 g of 30% hydrochloric acid; gradient: 0 min 10% A→4 min 90% A→9 min 90% A; oven: 50° C.; flow rate: 0.6 ml/min; UV detection: 210 nm.

Method C:

Instrument: Micromass Quattro LCZ, HP 1100; column: Symmetry C 18, 50 mm×2.1 mm, 3.5 μm; eluent A: acetonitrile+0.1% formic acid, eluent B: water+0.1% formic acid; gradient: 0 min 10% A→4 min 90% A→6 min 90% A; oven: 40° C.; flow rate: 0.5 ml/min; UV detection: 208–400 nm.

Method D:

Instrument: Micromass Platform LCZ, HP 1100; column: Symmetry C 18, 50 mm×2.1 mm, 3.5 μm; eluent A: acetonitrile+0.1% formic acid, eluent B: water+0.1% formic acid; gradient: 0 min 10% A→4 min 90% A→6 min 90% A; oven: 40° C.; flow rate: 0.5 ml/min; UV detection: 208–400 nm.

Method E:

Instrument: Finnigan MAT 900S, TSP: P4000, AS3000, UV3000HR; column: Symmetry C 18, 150 mm×2.1 mm, 5.0 μm; eluent A: acetonitrile, eluent B: water+0.3 g of 30% hydrochloric acid; gradient: 0 min 10% A→3 min 90% A→6 min 90% A; oven: 50° C.; flow rate: 0.9 ml/min; UV detection: 210 nm.

GC/MS

| | |
|---|---|
| Carrier gas: | Helium |
| Flow rate: | 1.5 ml/min |
| Starting temperature: | 60° C. |
| Temperature gradient: | 14° C./min up to 300° C., then 1 min const. 300° C. |
| column: | HP-5 30 m × 320 μm × 0.25 μm (film thickness) |
| Starting time: | 2 min |
| Front injector temp.: | 250° C. |

Starting Compounds:

EXAMPLE I

Step 1

Ethyl 5-amino-1-(2-fluorobenzyl)pyrazole-3-carboxylate

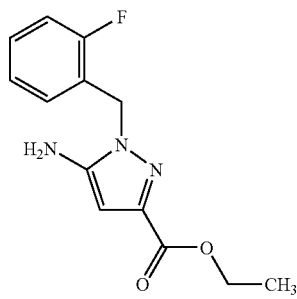

111.75 g (75 ml, 0.98 mol) of trifluoroacetic acid are added to 100.00 g (0.613 mol) of the sodium salt of ethyl cyanopyruvate (prepared in analogy to Borsche and Manteuffel, Liebigs Ann. 1934, 512, 97) while stirring efficiently in 2.5 l of dioxane at room temperature under argon, and the mixture is stirred for 10 min, during which most of the precursor dissolves. Then 85.93 g (0.613 mol) of 2-fluorobenzyl-hydrazine are added, and the mixture is boiled overnight. After cooling, the sodium trifluoroacetate crystals which have separated out are filtered off with suction and washed with dioxane, and the remaining crude solution is reacted further.

Step 2

Ethyl 1-(2-fluorobenzyl)-1H-pyrazolo[3,4-b]pyridine-3-carboxylate

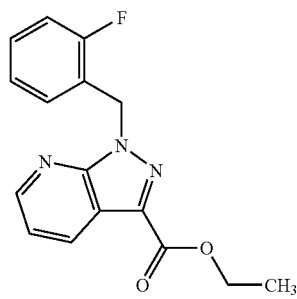

The solution obtained in step 1 is mixed with 61.25 ml (60.77 g, 0.613 mol) of dimethylaminoacrolein and 56.28 ml (83.88 g, 0.736 mol) of trifluoroacetic acid and boiled under argon for 3 days. The solvent is then evaporated in vacuo, and the residue is poured into 2 l of water and extracted three times with 1 l of ethyl acetate each time. The combined organic phases are dried with magnesium sulfate and concentrated in vacuo. Chromatography is carried out on 2.5 kg of silica gel, eluting with a toluene/toluene-ethyl acetate=4:1 gradient.

Yield: 91.6 g (49.9% of theory over two stages).
M.p.: 85° C.
$R_f$ (silica gel, toluene/ethyl acetate 1:1): 0.83

Step 3

1-(2-Fluorobenzyl)-1H-pyrazolo[3,4-b]pyridine-3-carboxamide

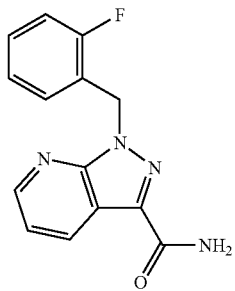

10.18 g (34 mmol) of the ester obtained in step 2 are introduced into 150 ml of methanol saturated with ammonia at 0–10° C. Stirring at room temperature for two days is followed by concentration in vacuo.

$R_f$ (silica gel, toluene/ethyl acetate 1:1): 0.33

Step 4

3-Cyano-1-(2-fluorobenzyl)-1H-pyrazolo[3,4-b]pyridine

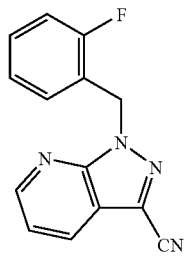

36.1 g (133 mmol) of 1-(2-fluorobenzyl)-1H-pyrazolo[3,4-b]pyridine-3-carboxamide from step 3 are dissolved in 330 ml of THF, and 27 g (341 mmol) of pyridine are added. Then, over the course of 10 min, 47.76 ml (71.66 g, 341 mmol) of trifluoroacetic anhydride are added, during which the temperature rises to 40° C. The mixture is stirred at room temperature overnight. The mixture is then poured into 1 l of water and extracted three times with 0.5 l of ethyl acetate each time. The organic phase is washed with saturated sodium bicarbonate solution and with 1 N HCl, dried with MgSO$_4$ and concentrated in vacuo.

Yield: 33.7 g (100% of theory)
M.p.: 81° C.
$R_f$ (silica gel, toluene/ethyl acetate 1:1): 0.74

Step 5

1-(2-Fluorobenzyl)-1H-pyrazolo[3,4-b]pyridine-3-carboximidamide

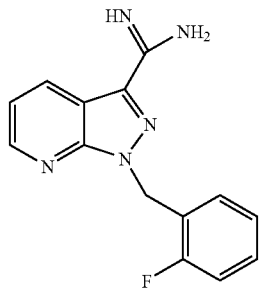

108.00 g (0.43 mol) of 1-(2-fluorobenzyl)-1H-pyrazolo[3,4-b]pyridine-3-carbonitrile (example I, step 4) are dissolved in one liter of methanol and added dropwise to a solution of 94.73 g (1.67 mol; purity: 95%) of sodium methoxide in 3 l of methanol. After stirring at RT for 2 hours, 28.83 g (0.54 mol) of ammonium chloride are added, and subsequently 100.03 g (1.67 mol) of glacial acetic acid are added dropwise. This solution is stirred under reflux overnight. The solvent is removed in vacuo, the residue is twice suspended in acetone and the insoluble solid is filtered off with suction. The latter is dissolved in 1.5 l of ethyl acetate, and 590 ml of an aqueous 20% strength sodium carbonate solution are added. Stirring for 20 minutes is followed by dilution with 200 ml of 1N sodium hydroxide solution. The organic phase is washed with saturated aqueous sodium chloride solution, dried over magnesium sulfate and filtered. The solvent is removed in vacuo. 99.10 g (86% of theory) of the product are obtained.

LC/MS (method B): $R_t$=2.25 min.
MS (ESIpos): m/z=270 (M+H)$^+$
$^1$H-NMR (300 MHz, DMSO-d$_6$): δ=5.79 (s, 2H), 6.54 (br s, 3H), 7.09–7.18 (m, 2H), 7.23 (t, 1H), 7.31–7.41 (m, 2H), 8.62 (d, 1H), 8.69 (d, 1H).

Step 6

3-(5-Bromo-2-pyrimidinyl)-1-(2-fluorobenzyl)-1H-pyrazolo[3,4-b]pyridine

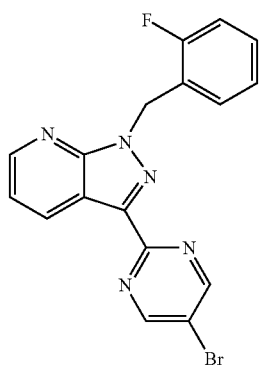

10.09 g (66.84 mmol) of 2-bromomalonaldehyde are added to a solution of 15.00 g (55.70 mmol) of 1-(2- fluorobenzyl)-1H-pyrazolo[3,4-b]pyridine-3-carboximida-mide (example I, step 5) in 200 ml of glacial acetic acid and stirring at 100° C. for 2 hours. The solvent is removed in vacuo. The residue is purified by chromatography on silica gel (eluent: DCM/methanol 40:1 to 30:1). 9.51 g (44% of theory) of the product are obtained.

HPLC: $R_t$=4.85 min.

LC/MS (method C): $R_t$=4.57 min.

MS (ESIpos): m/z=385 (M+H)$^+$ $^1$H-NMR (300 MHz, DMSO-d$_6$): δ=5.87 (s, 2H), 7.17 (q, 1H), 7.21–7.30 (m, 2H), 7.37 (q, 1H), 7.45 (dd, 1H), 8.70 (d, 1H), 8.82 (d, 1H), 9.13 (s, 2H).

EXAMPLE II

Step 1

7-Benzyl-3-phenylsulfonyl-9-oxa-3;7-diazabicyclo [3.3.1]nonane

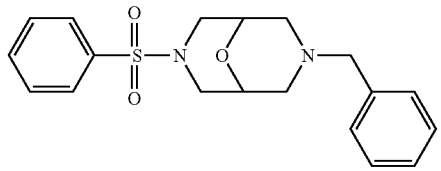

104.00 g (0.2 mol) of N-phenylsulfonyl-2,6-bisiodomethylmorpholine [Stetter, H.; Meissner, H.-J. Chem. Ber. 96, 2827 (1963)] are heated with 64.00 g (0.6 mol) of benzylamine in 1 l of xylene under reflux overnight. The benzylammonium iodide is filtered off with suction, the filtrate is concentrated, and the residue is recrystallized from ethanol. 32 g (44.6% of theory) of the product are obtained.

M.p.: 185–186° C.

Step 2

7-Benzyl-9-oxa-3,7-diazabicyclo[3.3.1]nonane

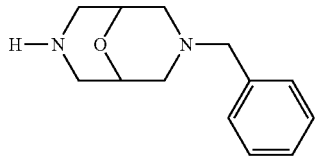

10.00 g (0.25 mol) of lithium aluminum hydride are introduced into 300 ml of absolute tetrahydrofuran and heated to reflux, and 18.00 g (50 mmol) of 7-benzyl-3-phenylsulfonyl-9-oxa-3,7-diazabicyclo[3.3.1]nonane, dissolved in 150 ml of absolute tetrahydrofuran, are added dropwise. The mixture is boiled under reflux for 48 hours, 10 ml portions of water, 15% strength potassium hydroxide solution and again water are added dropwise, and the organic salts are filtered off with suction and extracted by boiling twice with tetrahydrofuran. The tetrahydrofuran solutions are concentrated, and the residue is distilled under high vacuum. 5.30 g (43.5% of theory) of the product are obtained Boiling point: 110° C./0.1 mbar Step 3 tert-Butyl 7-benzyl-9-oxa-3,7-diazabicyclo[3.3.1] nonane-3-carboxylate

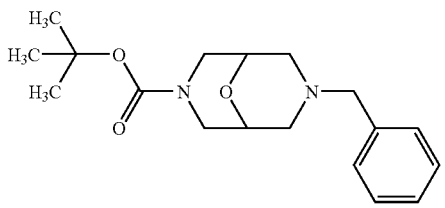

1.00 g of sodium hydroxide in 5 ml of water is added to 5.00 g (23 mmol) of 7-benzyl-9-oxa-3,7-diazabicyclo[3.3.1] nonane in 25 ml of tert-butanol, and 5.30 g (24 mmol) of di-tert-butyl pyrocarbonate are added dropwise. The mixture is stirred at room temperature overnight, 50 ml of water are added, three chloroform extractions and drying over magnesium sulfate are carried out, the desiccant is filtered off with suction, the filtrate is concentrated, and the crystalline residue is stirred with n-hexane. The crystals are filtered off with suction and dried in air. 5.80 g of the product (73% of theory) are obtained.

M.p.: 100–102° C.

Step 4 tert-Butyl 9-oxa-3,7-diazabicyclo[3.3.1]nonane-3-carboxylate

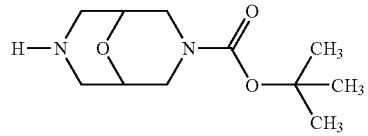

5.60 g (17.6 mmol) of tert-butyl 7-benzyl-9-oxa-3,7-diazabicyclo[3.3.1]nonane-3-carboxylate are dissolved in 100 ml of ethanol, 1.00 g of 10% palladium on activated carbon is added, and hydrogenation is carried out at 100° C. and 100 bar. The catalyst is filtered off with suction, and the filtrate is concentrated, whereupon 3.80 g (94.5% of theory) of pure product crystallize out.

M.p.: 93–95° C.

EXAMPLE III

Step 1

1-Benzyl-3-hydroxy-3-(2-hydroxyethylaminomethyl)pyrrolidine

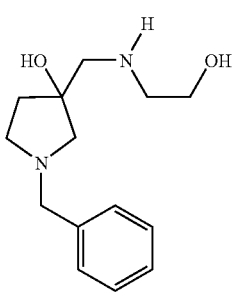

32.7 g (0.17 mol) of 5-benzyl-1-oxa-5-azaspiro[4.2]heptane (U.S. Pat. No. 4,508,724) are added dropwise to 31.0 g (0.52 mol) of ethanolamine in 250 ml of water, and the mixture is stirred at room temperature overnight. It is extracted with diethyl ether, the aqueous phase is concentrated, and the residue is distilled under high vacuum. 42.1 g (95.9% of theory) of the product are obtained.

Boiling point: 180–190° C./0.1 mbar

Step 2

7-Benzyl-1-oxa-4,7-diazaspiro[5.4]decane

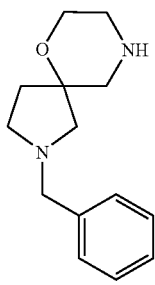

85.0 g (340 mmol) of 1-benzyl-3-hydroxy-3-(2-hydroxyethylaminomethyl)-pyrrolidine are dissolved in a mixture of 280 ml of concentrated sulfuric acid and 140 ml of water and heated at 180° C. overnight. The mixture is made alkaline with 45% strength sodium hydroxide solution, precipitated salts are dissolved in water, and the solution is extracted five times with 200 ml of chloroform each time. The organic phases are dried over potassium carbonate, the desiccant is removed, and the solution is concentrated. The residue is distilled under high vacuum. 60.0 g (76% of theory) of the product are obtained.

Boiling point: 125° C./0.08 mbar

Step 3 tert-Butyl 7-benzyl-1-oxa-4,7-diazaspiro[5.4]decane-4-carboxylate

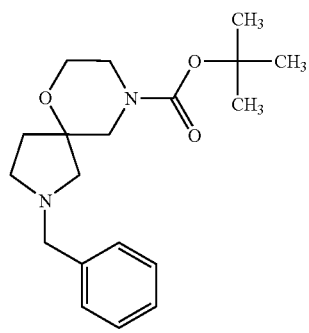

2.0 g of sodium hydroxide in 25 ml of water are added to 10.3 g (47 mmol) of 7-benzyl-1-oxa-4,7-diazaspiro[5.4]decane in 30 ml of tert-butanol, and 11.0 g (50 mmol) of di-tert-butyl pyrocarbonate are added dropwise. The mixture is stirred at room temperature overnight, 50 ml of water are added, three chloroform extractions and drying over potassium carbonate are carried out, the desiccant is filtered off with suction, the filtrate is concentrated, and the residue is distilled under high vacuum. 13.8 g of the product (88% of theory) are obtained.

Boiling point: 160° C./0.3 mbar

Step 4 tert-Butyl 1-oxa-4,7-diazaspiro[5.4]decane-4-carboxylate

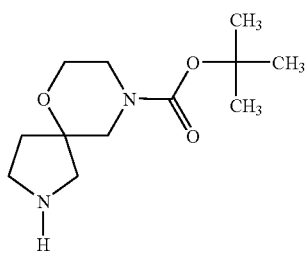

13.7 g (41 mmol) of tert-butyl 7-benzyl-1-oxa-4,7-diazaspiro[5.4]decane-4-carboxylate are dissolved in 300 ml of methanol, 3.0 g of 10% palladium on activated carbon are added, and hydrogenation is carried out at 100° C. and 100 bar. The catalyst is filtered off with suction, the filtrate is concentrated, and residue is distilled under high vacuum. 7.6 g (75% of theory) of the product are obtained.

Boiling point: 113° C./0.07 mbar

EXAMPLE IV

Step 1

10-Oxa-4-azatricyclo[5.2.1.0$^{2,6}$] decane-3,5-dione

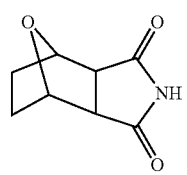

This compound can be obtained by Diels-Alder reaction of furan with maleimide, for example in analogy to Fisera, L., Melnikov, J., Pronayova, N., Ertl, P., Chem. Pap. 1995, 49 (4), 186–191.

Step 2

10-Oxa-4-azatricyclo[5.2.1.0$^{2,6}$]decane

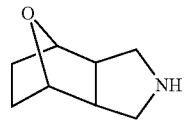

5.00 g (29.91 mmol) of 10-oxa-4-azatricyclo[5.2.1.0$^{2,6}$] decane-3,5-dione (example IV, step 1) were suspended in 150 ml of absolute THF under argon and cooled in an ice bath. 2.27 g (59.82 mmol) of lithium aluminum hydride are added in portions, and the mixture is stirred at 0° C. overnight. The reaction solution is hydrolyzed with saturated sodium chloride solution and distilled water, the resulting suspension is filtered, and the solid is washed with ethyl acetate. The organic phase of the filtrate is separated off, and the aqueous phase is extracted once more with ethyl acetate. The combined organic phases are dried and filtered, and the solvent is removed in vacuo. The residue is suspended in diethyl ether, filtered, washed with diethyl ether and dried. 730 mg (13% of theory) of the product are obtained.

GC/MS: $R_t$=6.22 min.

MS (EI): m/z=139 (M)$^+$ $^1$H-NMR (200 MHz, DMSO-d$_6$): δ=1.30–1.60 (m, 4H), 2.06–2.22 (quintet, 2H), 2.26–2.40 (dd, 2H), 2.81–2.98 (dd, 2H), 4.11–4.22 (t, 2H).

EXAMPLE V

Decahydropyrrolo[3,4-b]pyrrolizidine

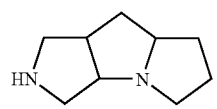

The preparation of this compound is described in: Schenke, Th., Petersen, U., U.S. Pat. No. 5,071,999.

EXAMPLE VI

Step 1

2-Benzyl-2,5-diazabicyclo [2.2.1]heptane

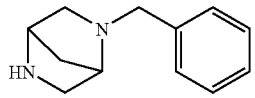

The preparation of this compound is described in: Portoghese, P. S., Mikhail, A. A., J. Org. Chem. 31 (1966), 1059.

Step 2 tert-Butyl 5-benzyl-2,5-diazabicyclo[2.2.1]heptane-2-carboxylate

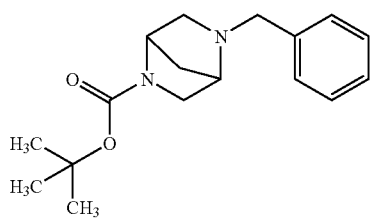

This compound is prepared in analogy to the method of example III, step 3.

Step 3 tert-Butyl 2,5-diazabicyclo[2.2.1]heptane-2-carboxylate

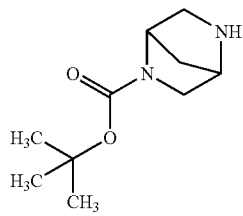

This compound is prepared in analogy to the method of example III, step 4.

Step 4 tert-Butyl 5{2-[1-(2-fluoroenzyl)-1H-pyrazolo[3,4-b]pyridin-3-yl]-5-pyrimidinyl}-2,5-diazabicyclo[2.2.1]heptane-2-carboxylate

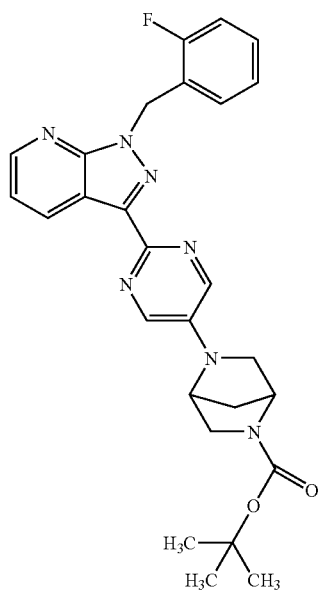

95 mg (0.85 mmol) of thoroughly dried potassium tert-butoxide are introduced into a previously heat-dried and evacuated apparatus under argon. 18 mg (0.02 mmol) of tris(dibenzylideneacetone)dipalladium, 48 mg (0.08 mmol) of rac-BINAP and 300 mg (0.77 mmol) of 3-(5-bromo-2-pyrimidinyl)-1-(2-fluorobenzyl)-1H-pyrazolo-[3,4-b]pyridine (example I, step 6) are successively added, and the apparatus is again evacuated and flushed with argon. The reagents are suspended in 40 ml of absolute toluene and then 460 mg (2.32 mmol) of tert-butyl-2,5-diazabicyclo[2.2.1]heptane-2-carboxylate (example VI, step 3) are added to the reaction mixture. The latter is stirred at 60° C. overnight.

The solvent is removed in vacuo, and the residue is purified by preparative HPLC. 327 mg (84% of theory) of the product are obtained.

LC/MS (method C): $R_t$=4.50 min.

MS (ESIpos): m/z=502.1 (M+H)$^+$ $R_f$=0.38 (DCM/methanol 20:1)

$^1$H-NMR (300 MHz, DMSO-d$_6$): δ=1.37 (d, 9H), 1.96 (s, 2H), 3.21 (t, 2H), 3.30–3.45 (m, 1H), 3.64 (br d, 1H), 4.51 (br d, 1H), 4.78 (s, 1H), 5.81 (s, 2H), 7.08–7.53 (m, 5H), 8.38 (s, 2H), 8.63 (d, 1H), 8.82 (d, 1H).

The examples listed in the following table can be prepared from the appropriate starting compounds in analogy to the method of example VI described above:

| Ex. No. | Structure | Analytical data |
|---|---|---|
| VII | 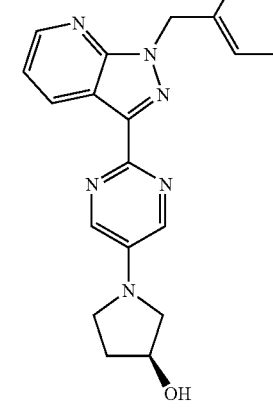 | LC/MS(method A): $R_t$=2.95 min. MS(ESIpos): m/z=532(M+H)$^+$ $R_f$=0.41(DCM/methanol 20:1) $^1$H-NMR(300 MHz, DMSO-d$_6$): δ=3.22(br d, 3H), 3.41(s, 10H), 3.85–4.05(m, 5H), 4.14(d, 1H), 5.87(s, 2H), 7.10–7.27(m, 3H), 7.31–7.43 (m, 2H), 8.53(s, 2H), 8.62(d, 1H), 8.80(d, 1H). |
| VIII | 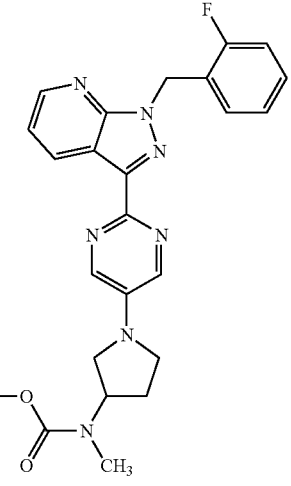 | LC/MS(method A): $R_t$=3.29 min. MS(ESIpos): m/z=546(M+H)$^+$ $^1$H-NMR(200 MHz, DMSO-d$_6$): δ=1.40(s, 9H), 1.92–2.24(m, 2H), 3.32–3.53 (m, 5H), 3.68(br s, 2H), 4.21(br s, 3H), 5.81(s, 2H), 7.10–7.45(m, 5H), 8.27(s, 2H), 8.62(d, 1H), 8.83(d, 1H). |
| IX | 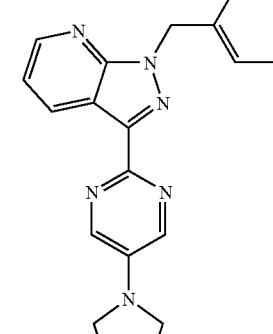 | $^1$H-NMR(400 MHz, DMSO-d$_6$): δ=2.01(br s, 1H), 2.05–2.18(m, 1H), 3.29(d, 1H), 3.45–3.62(m, 3H), 4.51(s, 1H), 5.85(s, 2H), 7.15–7.31(m, 3H), 7.34–7.57 (m, 2H), 8.30(s, 2H), 8.68(d, 1H), 8.88(d, 1H). |
| X | 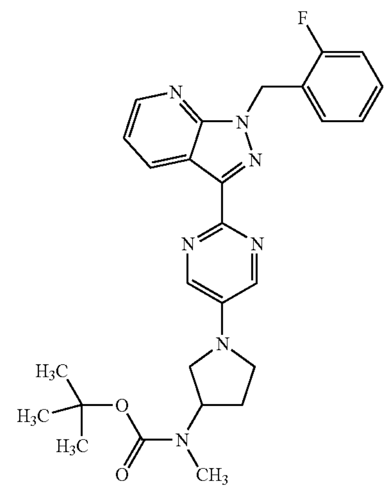 | LC/MS(method D): $R_t$=4.79 min. MS(ESIpos): m/z=504.4 (M+H)$^+$ $^1$H-NMR(200 MHz, DMSO-d$_6$): δ=1.43(s, 9H), 2.04–2.22(m, 2H), 3.28–3.44 (m, 1H), 3.46–3.73(m, 3H), 4.82(br t, 1H), 5.81(s, 2H), 7.10–7.43(m, 5H), 8.29(s, 2H), 8.63(d, 1H), 8.81(d, 1H). |
| XI | 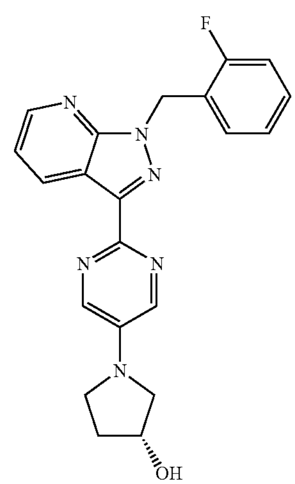 | LC/MS(method A): $R_t$=2.46 min. MS(ESIpos): m/z=391(M+H)$^+$ $^1$H-NMR(200 MHz, DMSO-d$_6$): δ=1.85–2.19(m, 2H), 3.24(d, 1H), 3.40–3.59(m, 3H), 4.46(s, 2H), 5.81(s, 2H), 7.09–7.45(m, 5H), 8.26(s, 2H), 8.62(d, 1H), 8.83 (d, 1H). |

EXAMPLE XII

Step 1

2,5-Anhydro-3,4-dideoxy-1,6-bis-O-[(4-methylphenyl)sulfonyl]hexitol

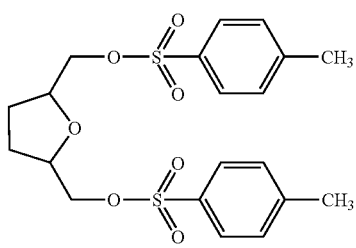

34.0 g (261 mmol) of 2,5-bis(hydroxymethyl)tetrahydrofuran are dissolved in 260 ml of dichloromethane. A solution of 99.0 g (521 mmol) of p-toluenesulfonyl chloride in 52 ml of pyridine and 130 ml of dichloromethane is added dropwise thereto. After stirring at room temperature for 24 hours, the precipitate is filtered off with suction and washed with dichloromethane. The filtrate and the washing phases are combined, washed with dilute hydrochloric acid and then with saturated aqueous sodium bicarbonate solution, dried over magnesium sulfate and evaporated to dryness. The crude product is recrystallized from ethanol.

Yield: 112 g (98% of theory)
M.p.: 125° C.
MS (CIpos): m/z=441 (M+H)$^+$.

Step 2

3-Benzyl-8-oxa-3-azabicyclo[3.2.1]octane

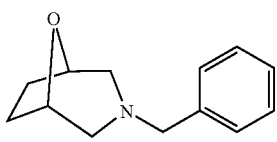

112 g (250 mmol) of 2,5-anhydro-3,4-dideoxy-1,6-bis-O-[(4-methylphenyl)sulfonyl]-hexitol from step 1 and 90.7 g (840 mmol) of benzylamine in 500 ml of toluene are heated under reflux for 20 hours. The precipitate is then filtered off with suction and washed with toluene. The combined toluene phases are concentrated in a rotary evaporator and distilled in vacuo. After a benzylamine fore-run, the product is obtained.

Yield: 28.2 g (54% of theory)
Boiling point: 96–99° C./8 mbar
MS (CIpos): m/z=204 (M+H)$^+$.

Step 3

8-Oxa-3-azabicyclo[3.2.1]octane hydrochloride

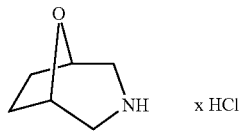

28.20 g (136 mmol) of 3-benzyl-8-oxa-3-azabicyclo[3.2.1]octane from step 2 are dissolved in 200 ml of ethanol, a 5.00 g of palladium on activated carbon (10%) are added, and hydrogenation is carried out with 100 bar of hydrogen in an autoclave at 100° C. The catalyst is filtered off with suction and the mother liquor is mixed with 11.9 ml of concentrated hydrochloric acid and concentrated in a rotary evaporator. Acetone is added to the residue, and the resulting precipitate is filtered off with suction and dried over phosphorus pentoxide.

Yield: 17.0 g (84% of theory)
M.p.: 209–221° C.
MS (CIpos): m/z=114 (M+H)$^+$.

Step 4

8-Oxa-3-azabicyclo[3.2.1]octane

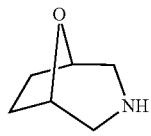

4.15 g (27.7 mmol) of 8-oxa-3-azabicyclo[3.2.1]octane hydrochloride from step 3 are suspended in 100 ml of dichloromethane, and a solution of 3.23 g (30.5 mmol) of sodium carbonate in 30 ml of water is added. The mixture is stirred at room temperature for 30 minutes. The organic phase is then separated off, washed with 30 ml of saturated aqueous sodium chloride solution and evaporated to dryness in a rotary evaporator. The residue is dried in vacuo.

Yield: 2.46 g (76% of theory).

Step 5

Diethyl 2-(8-oxa-3-azabicyclo[3.2.1]oct-3-yl)malonate

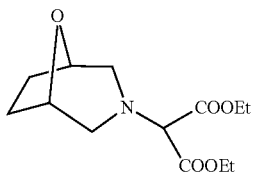

4.72 g (19.8 mmol) of diethyl 2-bromomalonate are introduced into 30 ml of acetonitrile. Then 3.82 g (27.7 mmol) of potassium carbonate and 2.46 g (21.7 mmol) of 8-oxa-3-azabicyclo[3.2.1]octane from step 4 are added. The suspension is stirred at 50° C. overnight. This is followed by filtration with suction and evaporation of the filtrate to dryness in a rotary evaporator. The residue is employed without further purification in the next stage.

Yield: 5.09 g (95% of theory).

Step 6

2-[1-(2-Fluorobenzyl)-1H-pyrazolo[3,4-b]pyridin-3-yl]-5-(8-oxa-3-azabicyclo-[3.2.1]oct-3-yl)-4,6-pyrimidinediol

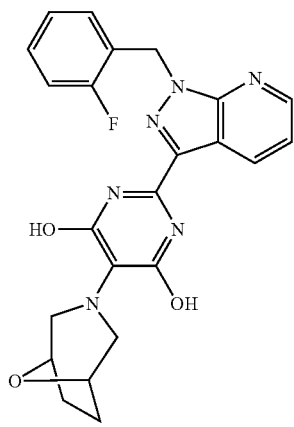

0.50 g (1.11 mmol) of 1-(2-fluorobenzyl)-1H-pyrazolo[3,4-b]pyridine-3-carboximidamide (example I, step 5) are suspended in 40 ml of toluene. Then 1.40 g (5.16 mmol) of diethyl 2-(8-oxa-3-azabicyclo[3.2.1]oct-3-yl)malonate from step 5 are added. The mixture is stirred at 140° C. overnight. The solid is then filtered off with suction, washed with diethyl ether dried in vacuo.

Yield: 515 mg (24% of theory)

MS (ESIpos): m/z=449 (M+H)$^+$.

Step 7

3-[4,6-Dichloro-5-(8-oxa-3-azabicyclo[3.2.1]oct-3-yl)-2-pyrimidinyl]-1-(2-fluorobenzyl)-1H-pyrazolo[3,4-b]pyridine

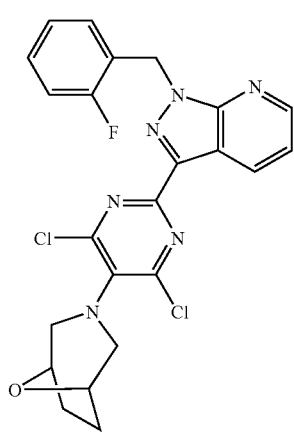

1.33 g (4.69 mmol) of 2-[1-(2-fluorobenzyl)-1H-pyrazolo[3,4-b]pyridin-3-yl]-5-(8-oxa-3-azabicyclo[3.2.1]oct-3-yl)- 4,6-pyrimidinediol from step 6 are dissolved in 5 ml (53.6 mmol) of phosphorus oxychloride. 3 drops of N,N-dimethylformamide are added to the mixture, and it is heated under reflux for 3 hours. After cooling to room temperature and concentration in a rotary evaporator, the residue is dried under high vacuum. The crude product is purified by preparative HPLC.

Yield: 252 mg (46% of theory)

LC/MS (method E): $R_t$=3.58 min

MS (ESIpos): m/z=485 (M+H)$^+$ $^1$H-NMR (300 MHz, DMSO-$d_6$): δ=1.80–1.92 (m, 2H), 2.11–2.20 (m, 2H), 2.66 (d, 2H), 3.54 (dd, 2H), 4.35 (s, 2H), 5.88 (s, 2H), 7.10–7.28 (m, 3H), 7.31–7.41 (m, 1H), 7.55 (dd, 1H), 8.70–8.80 (m, 2H).

EXAMPLE XIII

1-Methyloctahydropyrrolo[3,4-d][1,3]oxazine

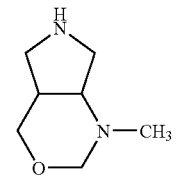

The preparation of this compound is described in: Petersen, U. et al., EP 350 733.

EXAMPLE XIV tert-Butyl (3R)-3-hydroxy-1-piperidincarboxylate

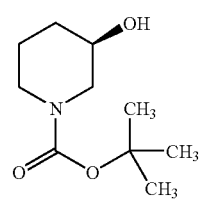

26.80 g (0.20 mol) of (3R)-3-piperidinol hydrochloride are introduced into 150 ml of THF and, while cooling in an ice bath, 65.04 g (0.64 mol) of triethylamine are added. The mixture is stirred at the same temperature for 20 minutes and then 70 ml of di(tert-butyl) dicarbonate are introduced into the solution, and the mixture is stirred at RT overnight. The reaction solution is extracted with 1N hydrochloric acid. The organic phase is washed with saturated aqueous sodium chloride solution, dried and filtered, and the solvent is removed in vacuo. 36.00 g (90% of theory) of the product are obtained.

GC/MS: $R_t$=12.43 min.

MS (EI): m/z=201 (M)$^+$ $^1$H-NMR (400 MHz, DMSO-$d_6$): δ=1.21–1.32 (m, 2H), 1.34–1.42 (m, 9H), 1.48 (s, 1H), 1.58–1.65 (m, 1H), 1.77–1.88 (m, 1H), 2.78 (br t, 1H), 3.33–3.41 (m, 1H), 3.58–3.63 (dt, 1H), 3.75 (br d, 1H), 4.82 (s, 1H).

EXAMPLE XV tert-Butyl (3R)-3-hydroxy-1-pyrrolidinecarboxylate

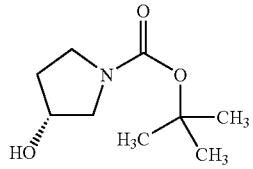

This compound is obtained from 3-(R)-hydroxypyrrolidine in analogy to the method of example XIV.

EXAMPLE XVI

Step 1 tert-Butyl (3S,4S)-3,4-dihydroxy-1-pyrrolidinecarboxylate

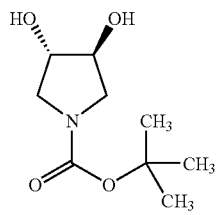

This compound is prepared as described in: Nagel, U., Angew. Chem. 96 (1984), 425.

Step 2 tert-Butyl (3S,4S)-3,4-dimethoxy-1-pyrrolidinecarboxylate

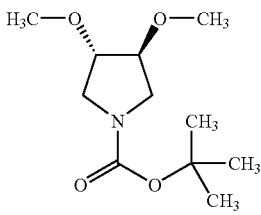

2.60 g (12.73 mmol) of tert-butyl (3S,4S)-3,4-dihydroxy-1-pyrrolidinecarboxylate (example XVI, step 1) are dissolved in 60 ml of absolute DMF under argon and, while cooling in an ice bath, 0.74 g (29.42 mmol; 95% pure) of sodium hydride is added in portions. The mixture is stirred at 0° C. for 10 minutes and then, at the same temperature, 4.00 g (28.14 mmol) of iodomethane are added dropwise. The reaction mixture is stirred at Rt for 2 hours and then hydrolyzed by adding 20 ml of saturated aqueous sodium chloride solution and 80 ml of distilled water. The aqueous phase is extracted with ethyl acetate. The combined organic phases are washed with saturated aqueous sodium chloride solution, dried and filtered, and the solvent is removed under vacuum. The residue is purified by chromatography on silica gel (eluent: DCM/methanol 100:1). 2.39 (76% of theory) of the product are obtained.

LC/MS (method D): $R_t$=3.45 min.

MS (ESIpos): m/z=255 (M+H)$^+$ $^1$H-NMR (300 MHz, DMSO-d$_6$): δ=1.39 (s, 10H), 2.73 (s, 1H), 2.89 (s, 1H), 3.28 (s, 7H), 3.80 (br s, 2H).

Step 3

(3S,4S)-3,4-Dimethoxypyrrolidine

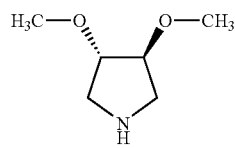

2.30 g (9.35 mmol; 94% pure) of tert-butyl (3S,4S)-3,4-dimethoxy-1-pyrrolidinecarboxylate (example XVI, step 2) are taken up in 50 ml of hydrochloric acid (4M in dioxane) and stirred at RT overnight. The solvent is removed in vacuo, and the residue is suspended in DCM, mixed with 1N sodium hydroxide solution and stirred at RT for 10 minutes. The phases are separated and the aqueous phase is extracted several times with DCM. The combined organic phases are extracted with saturated aqueous sodium chloride solution, dried and filtered, and the solvent is removed in vacuo. 872 mg (63% of theory) of the product are obtained.

GC/MS: $R_t$=4.76 min.

MS (CIpos): m/z=132 (M+H)$^+$ $^1$H-NMR (400 MHz, DMSO-d$_6$): δ=2.63 (dd, 4H), 2.89 (dd, 4H), 3.63 (q, 4H), 7.95 (s, 1H).

The examples listed in the following table can be prepared from the appropriate starting compounds in analogy to the method of example XVI described above:

| Ex. No. | Structure | Analytical data |
|---|---|---|
| XVII | ![structure] | GC/MS: $R_t$=3.14 min. MS(CIpos): m/z=133.1(M+H)$^+$ $^1$H-NMR(300MHz, DMSO-d$_6$): δ= 1.08–1.15(m, 3H), 1.58–1.85(m, 2H), 2.40–2.60(m, 1H), 2.71–2.91(m, 4H), 3.31–3.43(m, 2H), 3.92–4.00(m, 1H). |
| XVIII | ![structure] | GC/MS: $R_t$=6.77 min. MS(EIpos): m/z=116(M+H)$^+$. |

EXAMPLE XIX

Step 1

(3R)-3-[(Triethylsilyl)oxy]pyrrolidine

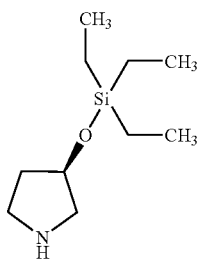

381 mg (2.53 mmol) of triethylchlorosilane are added to a solution, cooled in ice, of 200 mg (2.30 mmol) of (3R)-3-pyrrolidinol in 3 ml of absolute pyridine under argon. The reaction mixture is stirred at RT for one hour and is then mixed with 6 ml of distilled water and extracted with diethyl ether. The solvent of the organic phase is removed under vacuum, and the residue is thoroughly dried. 99 mg (21% of theory) of the product are obtained.

MS (DCI): m/z=219.2 (M+H)$^+$ $R_f$=0.39 (DCM/methanol 20:1)

$^1$H-NMR (200 MHz, DMSO-d$_6$): δ=0.58 (q, 6H), 0.92 (t, 9H), 1.81–2.02 (m, 1H), 2.85 (br d, 1H), 3.03–3.18 (m, 4H), 4.48 (br quintet, 1H), 8.52 (br s, 1H).

Step 2

1-(2-Fluorobenzyl)-3-(5-{(3R)-3-[(triethylsilyl)oxy]-1-pyrrolidinyl}-2-pyrimidinyl)-1H-pyrazol[3,4-b]pyridine

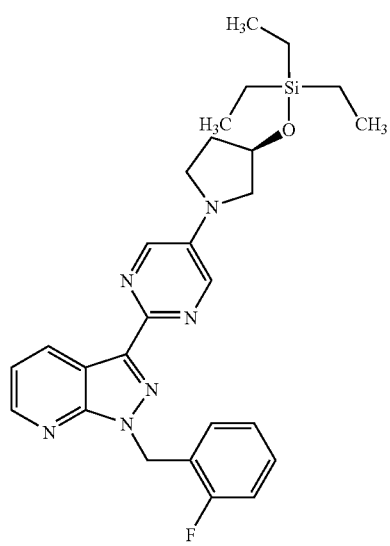

The compound is prepared in analogy to the method of example VI, step 4, apart from the following modifications. The reaction is carried out in absolute dioxane with sodium tert-butoxide instead of the corresponding potassium compound. Starting from 94 mg (0.25 mmol) of 3-(5-bromo-2-pyrimidinyl)-1-(2-fluorobenzyl)-1H-pyrazolo[3,4-b]pyridine (example I, step 6) and 99 mg (0.49 mmol) of (3R)-3-[(triethylsilyl)oxy]pyrrolidine (example XIX, step 1), 80 mg (65% of theory) of the product are obtained.

HPLC: $R_t$=3.98 min.

MS (ESIpos): m/z=505 (M+H)$^+$ $R_f$=0.32 (DCM/ethyl acetate 2:1)

$^1$H-NMR (300 MHz, DMSO-d$_6$): δ=0.61 (q, 6H), 0.94 (t, 9H), 1.24 (s, 1H), 1.89–2.02 (m, 1H), 2.08–2.22 (m, 1H), 3.47 (t, 2H), 3.59 (dd, 1H), 4.63 (s, 1H), 5.80 (s, 2H), 7.10–7.28 (m, 3H), 7.30–7.41 (m, 2H), 8.27 (s, 2H), 8.62 (d, 1H), 8.82 (d, 1H).

Step 3

(3R)-1-{2-[1-(2-Fluorobenzyl)-1H-pyrazolo[3,4-b]pyridin-3-yl]-5-pyrimidinyl}-3-pyrrolidinol

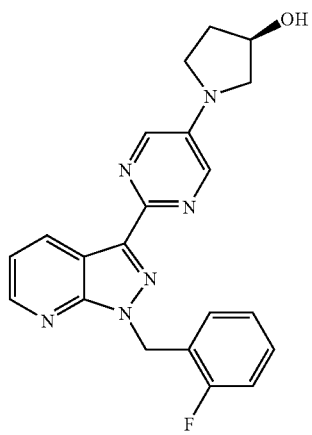

2.64 g (5.23 mol) of 1-(2-fluorobenzyl)-3-(5-{(3R)-3-[(triethylsilyl)oxy]-1-pyrrolidinyl}-2-pyrimidinyl)-1H-pyrazol[3,4-b]pyridine (example XIX, step 2) are dissolved in 50 ml of absolute THF under argon, and 2.19 g (8.37 mol) of a 1 molar tetrabutylammonium fluoride solution in THF are added. The solution is stirred at RT overnight. It is diluted with 50 ml of a 1:1 mixture of distilled water and ethyl acetate, and the aqueous phase is separated off and then extracted three times with ethyl acetate. The solvent of the combined organic phases is removed in vacuo, and the resulting crude product is chromatographed on silica gel (eluent: DCM/methanol 30:1). 1.64 g (80% of theory) of the product are obtained.

HPLC: $R_t$=4.02 min.

MS (ESIpos): m/z=391 (M+H)$^+$ $R_f$=0.42 (DCM/methanol 20:1)

$^1$H-NMR (300 MHz, DMSO-d$_6$): δ=1.40 (s, 1H), 1.89–2.17 (m, 2H), 3.42–3.58 (m, 3H), 4.46 (s, 1H), 5.04 (d, 1H), 5.80 (s, 2H), 7.10–7.28 (m, 3H), 7.30–7.42 (m, 2H), 8.25 (s, 2H), 8.62 (d, 1H), 8.83 (d, 1H).

The following examples XX and XXI can be obtained by reacting the appropriate halopyridines (4-chloro- or 3-bromopyridines) by either reacting them in analogy to the method in Saji, H.; Watanabe, A.; Magata, Y.; Ohmomo Y.; Kiyono, Y.; Yamada, Y.; Iida, Y.; Yonekura, Y.; Konishi, J.; Yokoyama, A. Chem. Pharm. Bull. 1997, 45, 284–290 with hexabutyldistannane with the addition of Pd(PPh$_3$)$_4$ in toluene, or lithiating them in analogy to the method of Garg, S.; Garg, P. K; Zalutsky, M. R.; Bioconjugate Chem. 1991, 2, 50–56 with buthyllithium and subsequently introducing the stannyl radical with chlorotributylstannane:

EXAMPLE XX

2-Fluoro-4-(tributylstannyl)pyridine

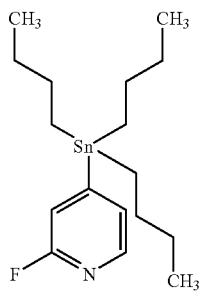

EXAMPLE XXI

2-Fluoro-3-(tributylstannyl)pyridine

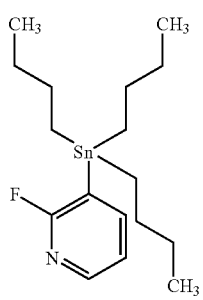

EXAMPLE XXII

5-Cyclopropyl-4-(tributylstannyl)isoxazole

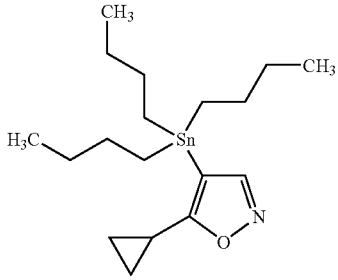

This compound can be prepared in analogous manner to the compounds of examples XX and XXI.

EXAMPLE XXIII

Ethyl 2-bromo-4-fluorobenzoate

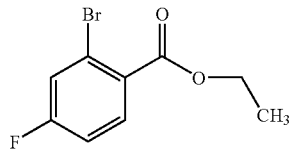

281 mg (2.21 mmol) of oxalyl chloride are added to a solution of 220 mg (1.01 mmol) of 2-bromo-4-fluorobenzoic acid in 5 ml of absolute toluene under argon, and the mixture is stirred at RT for 4 hours. The solvent is removed in vacuo, and the residue is taken up three times in DCM and the solvent is removed each time in vacuo. A yellow oil is obtained and is dissolved in a little DCM. 213 mg (2.10 mmol) of triethylamine and 2 ml of ethanol are added to the solution, and the mixture is stirred at RT for three hours. The reaction mixture is diluted with twice the volume of distilled water and extracted with DCM. The solvent of the organic phase is removed in vacuo, and the residue is chromatographed on silica gel (eluent: DCM/methanol 20:1). 100 mg (39% of theory) of the product are obtained.

HPLC: $R_t$=4.80 min.

MS (ESIpos): m/z=248 (M+H)$^+$ $^1$H-NMR (200 MHz, DMSO-d$_6$): δ=1.32 (t, 3H), 4.32 (q, 2H), 7.40 (t, 1H), 7.73 (dd, 1H), 7.81 (dd, 1H).

EXAMPLE XXIV 1-(2-Fluorobenzyl)-3-[5-(trimethylstannyl)-2-pyrimidinyl]-1H-pyrazolo[3,4-b]-pyridine

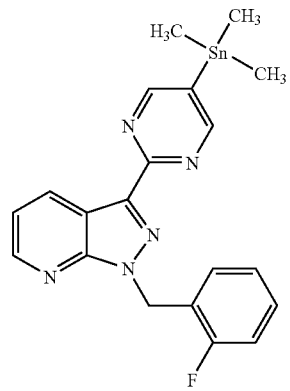

5.12 g (15.62 mmol) of 1,1,1,2,2,2-hexamethyldistannane and 0.59 g (0.83 mmol) of bis(triphenylphosphine)palladium(II) chloride are added to a solution of 2.00 g (5.21 mmol) of 3-(5-bromo-2-pyrimidinyl)-1-(2-fluorobenzyl)-1H-pyrazol[3,4-b]-pyridine (example I, step 6) in 75 ml of absolute dioxane under argon, and the mixture is stirred at 80–85° C. overnight. It is hydrolyzed by adding 40 ml of a 1 molar aqueous potassium fluoride solution and extracted three times with ethyl acetate. The combined organic phases are dried over magnesium sulfate and filtered, and the solvent is removed under vacuum. The crude product is purified on silica gel (eluent: cyclohexane/ethyl acetate 3:1). 1.56 g (60% of theory) of the product are obtained.

LC/MS (method D): $R_t$=5.20 min.

MS (ESIpos): m/z=469 (M+H)$^+$ $R_f$=0.75 (toluene/ethyl acetate 1:1)

$^1$H-NMR (200 MHz, DMSO-d$_6$): δ=0.39 (t, 9H), 5.87 (s, 2H), 7.10–7.49 (m, 5H), 8.68 (d, 1H), 8.87 (d, 1H), 8.90 (s, 3H).

EXAMPLE XXV

Ethyl 2-bromo-5-fluorobenzoate

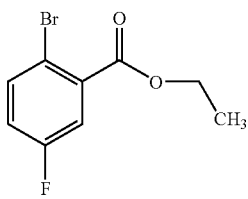

The compound is prepared in analogy to the method of example XXIII. 320 mg (34% of theory) of the product are obtained starting from 670 mg (3.06 mmol) of 2-bromo-5-fluorobenzoic acid.

HPLC: $R_t$=4.66 min.

MS (ESIpos): m/z=248 (M+H)$^+$ $R_f$=0.90 (DCM/methanol 20:1)

$^1$H-NMR (300 MHz, DMSO-d$_6$): δ=1.33 (t, 3H), 4.33 (q, 2H), 7.37 (t, 1H), 7.61 (dd, 1H), 7.81 (dd, 1H).

EXAMPLE XXVI

Step 1

1-Cyclopropyl-2-{2-[1-(2-fluorobenzyl)-1H-pyrazolo[3,4-b]pyridin-3-yl]-5-pyrimidinyl}ethanone

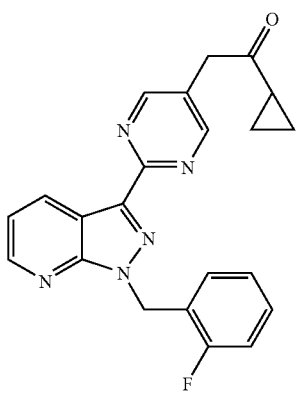

500 mg (5.2 mmol) of thoroughly dried sodium tert-butoxide are introduced into a heat-dried and evacuated apparatus under argon. 143 mg (0.16 mmol) of tris(dibenzylideneacetone)dipalladium, 243 mg (0.39 mmol) of rac-BINAP and 1000 mg (2.6 mmol) of 3-(5-bromo-2-pyrimidinyl)-1-(2-fluorobenzyl)-1 H-pyrazol[3,4-b]pyridine (example I, step 6) are successively added, and the apparatus is again evacuated and flushed with argon. The reagents are suspended in 40 ml of absolute dioxane, mixed with 438 mg (0.47 ml, 5.2 mmol) of cyclopropyl methyl ketone and heated to reflux for 2 hours. The solvent is removed in vacuo, and the residue is purified by chromatography on silica gel (eluent: DCM/methanol 20:1). 630 mg (57% of theory) of the product are obtained.

HPLC: $R_t$=4.53 min.

MS (ESIpos): m/z=388 (M+H)$^+$ $R_f$=0.51 (DCM/methanol 20:1)

$^1$H-NMR (300 MHz, DMSO-d$_6$): δ=0.92–1.02 (m, 4H), 2.20 (quintet, 1H), 4.12 (s, 2H), 5.87 (s, 2H), 7.16 (q, 1H), 7.22–7.49 (m, 3H), 7.42 (dd, 1H), 8.67 (d, 1H), 8.77 (s, 2H), 8.88 (d, 1H).

Step 2

(2E)-1-Cyclopropyl-3-(dimethylamino)-2-{2-[1-(2-fluorobenzyl)-1H-pyrazol[3,4-b]-pyridin-3-yl]-5-pyrimidinyl}-2-propen-1-one

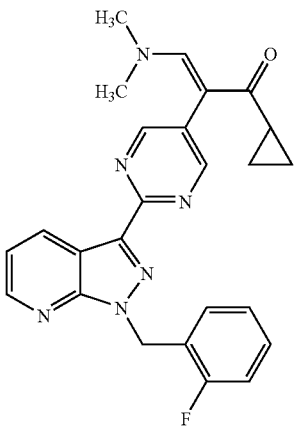

100 mg (0.26 mmol) of 1-cyclopropyl-2-{2-[1-(2-fluorobenzyl)-1H-pyrazolo[3,4-b]-pyridin-3-yl]-5-pyrimidinyl}ethanone (example XXVI, step 1) are added to a solution of 123 mg (1.03 mmol) of N-(dimethoxymethyl)-N,N-dimethylamine in 1 ml of DMF. The reaction mixture is stirred at 110° C. for 2 hours and then poured into distilled water. The precipitated solid is filtered off, washed with distilled water and dried. 93 mg (64% of theory) of the product are obtained and are directly reacted further without further purification.

HPLC: $R_t$=4.67 min.

MS (ESIpos): m/z=443 (M+H)$^+$ $^1$H-NMR (200 MHz, DMSO-d$_6$): δ=0.67–0.75 (m, 2H), 0.78–0.84 (m, 2H), 2.13–2.31 (m, 1H), 2.83 (s, 6H), 5.86 (s, 2H), 7.10–7.46 (m, 5H), 7.94 (s, 1H), 8.66 (s, 3H), 8.90 (d, 1H).

EXEMPLARY EMBODIMENTS

EXAMPLE 1

1-(2-Fluorobenzyl)-3-{5-[(1S,5R)-1,3,3-trimethyl-6-azabicyclo[3.2.1]oct-6-yl]-2-pyrimidinyl}-1H-pyrazol[3,4-b]pyridine

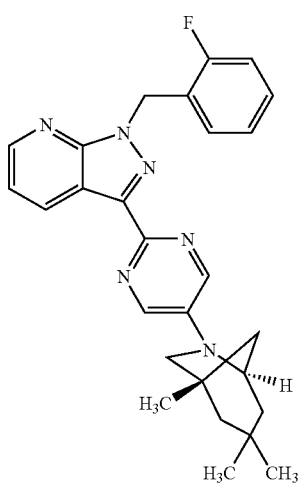

95 mg (0.85 mmol) of thoroughly dried potassium tert-butoxide are introduced into a heat-dried and evacuated apparatus under argon. 18 mg (0.02 mmol) of tris(dibenzylideneacetone)dipalladium, 48 mg (0.08 mmol) of rac-BINAP and 300 mg (0.77 mmol) of 3-(5-bromo-2-pyrimidinyl)-1-(2-fluorobenzyl)-1H-pyrazolo[3,4-b]pyridine (example I, step 6) are successively added, and the apparatus is again evaporated and flushed with argon. The reagents are suspended in 4.5 ml of absolute toluene and then 355 mg (2.32 mmol) of (1S,5R)-1,3,3-trimethyl-6-azabicyclo[3.2.1]octane are added to the reaction mixture. The latter is stirred at 60° C. overnight. The solvent is removed in vacuo, and the residue is purified by preparative HPLC. 73 mg (20% of theory) of the product are obtained.

LC/MS (method A): $R_t$=3.79 min.

MS (ESIpos): m/z=457 (M+H)$^+$ $R_f$=0.75 (DCM/methanol 20:1)

$^1$H-NMR (300 MHz, DMSO-d$_6$): δ=0.74 (s, 3H), 0.92 (s, 3H), 1.15 (s, 3H), 1.34 (d, 1H), 1.45–1.61 (m, 3H), 1.78 (br s, 1H), 1.91 (d, 1H), 3.18 (dd, 2H), 4.28 (br s, 1H), 5.79 (s, 2H), 7.09–7.26 (m, 4H), 7.30–7.42 (m, 1H), 8.21 (s, 2H), 8.61 (d, 1H), 8.82 (d, 1H).

The examples listed in the following table can be prepared from the appropriate starting compounds in analogy to the method of example I:

| Ex. No. | Structure | Analytical data |
|---|---|---|
| 2 | 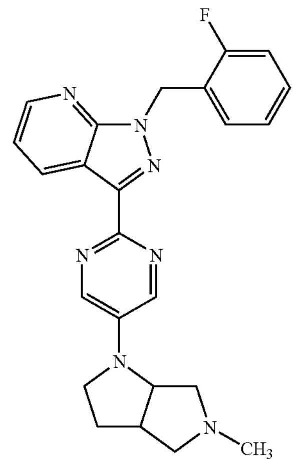 | LC/MS(method A): $R_t$= 1.70 min. MS(ESIpos): m/z= 430(M+H)$^+$ $^1$H-NMR(300MHz, DMSO-d$_6$): δ=1.95–2.24 (m, 2H), 2.79(s, 3H), 3.28–3.41(m, 3H), 3.49–3.75(m, 2H), 3.85(q, 1H), 4.56(q, 1H), 5.82(s, 2H), 7.10–7.29(m, 3H), 7.32–7.46(m, 2H), 8.34(d, 2H), 8.64(d, 1H), 8.83(d, 1H). |
| 3 | 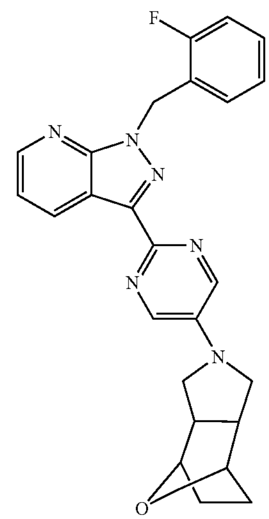 | LC/MS(method D): $R_t$= 4.22 min. MS(ESIpos): m/z= 443.4(M+H)$^+$. |
| 4 | 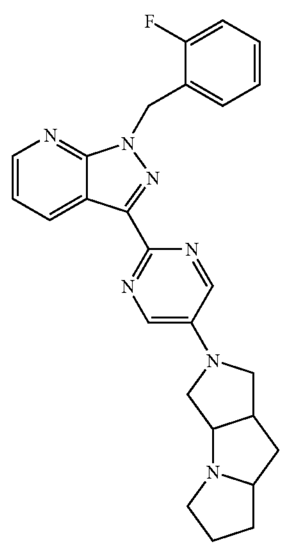 | LC/MS(method A): $R_t$= 1.82 min. MS(ESIpos): m/z= 446(M+H)$^+$ $^1$H-NMR(200MHz, DMSO-d$_6$): δ=1.70–2.32 (m, 4H), 3.26–3.70(m, 5H), 3.80–4.19(m, 4H), 4.34(br s, 2H), 5.82(s, 2H), 7.09–7.48(m, 5H), 8.30(s, 2H), 8.64(d, 1H), 8.84(d, 1H). |

| Ex. No. | Structure | Analytical data |
|---|---|---|
| 5 | 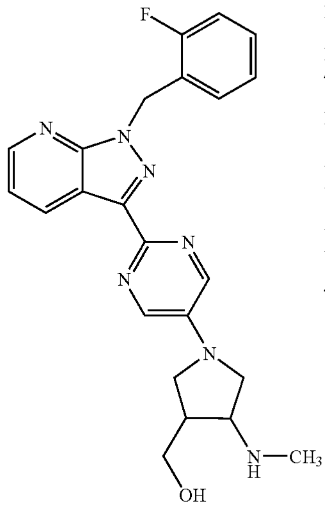 | LC/MS(method A): R$_t$= 1.67 min. MS(ESIpos): m/z= 434(M+H)$^+$ $^1$H-NMR(300MHz, DMSO-d$_6$): δ=1.53–1.68 (m, 1H), 1.69–1.84(m, 2H), 1.90–2.07(m, 1H), 2.63(q, 1H), 2.92 (quintet, 1H), 3.18(s, 3H), 3.19–3.30(m, 2H), 3.33–3.43(dd, 2H), 5.80 (s, 2H), 7.09–7.25(m, 4H), 7.33–7.46(m, 1H), 8.40(s, 2H), 8.62(d, 1H), 8.82(d, 1H). |
| 6 | 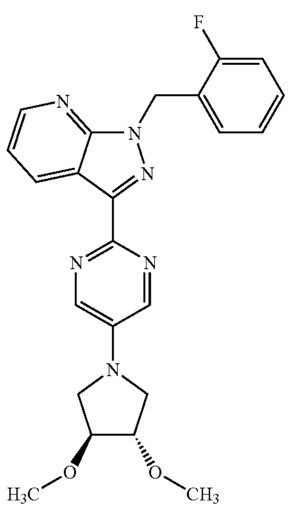 | LC/MS(method A): R$_t$= 2.65 min. MS(ESIpos): m/z= 435(M+H)$^+$ $^1$H-NMR(400MHz, DMSO-d$_6$): δ=3.36(s, 6H), 3.43–3.57(m, 4H), 4.04(s, 2H), 5.81(s, 2H), 7.13–7.27(m, 3H), 7.33–7.41(m, 2H), 8.29(s, 2H), 8.63(d, 1H), 8.82(d, 1H). |
| 7 | 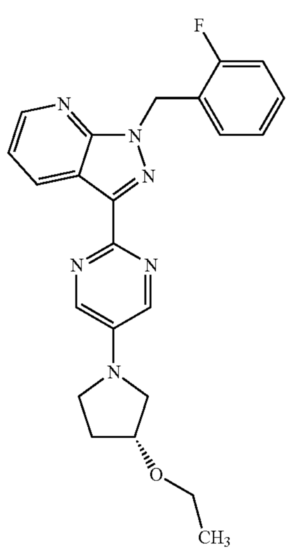 | LC/MS(method C): R$_t$= 4.43 min. MS(ESIpos): m/z= 419.3(M+H)$^+$ $^1$H-NMR(300MHz, DMSO-d$_6$): δ=1.12(t, 3H), 2.10(q, 2H), 3.36–3.58(m, 6H), 4.25(br s, 1H), 5.81(s, 2H), 7.08–7.42(m, 5H), 8.27(s, 2H), 8.63(d, 1H), 8.83(d, 1H). |
| 8 | | LC/MS(method D): R$_t$= 4.33 min. MS(ESIpos): m/z= 419.4(M+H)$^+$ $^1$H-NMR(300MHz, DMSO-d$_6$): δ=1.41–1.59 (m, 2H), 1.76–1.89(m, 1H), 1.90–2.02(m, 1H), 3.03–3.18(m, 2H), 3.30 (s, 3H), 3.45–3.61(m, 2H), 3.69–3.71(d, 1H), 5.80(s, 2H), 7.10–7.27 (m, 3H), 7.30–7.43(m, 2H), 8.62(d, 3H), 8.81(d, 1H). |

EXAMPLE 9

3-[5-(2,5-Diazabicyclo[2.2.1]hept-2-yl)-2-pyrimidinyl]-1-(2-fluorobenzyl)-1H-pyrazol-[3,4-b]pyridine

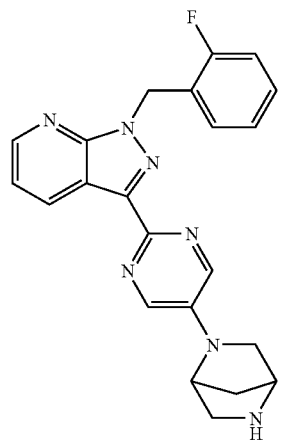

250 mg (0.50 mmol) of tert-butyl 5-{2-[1-(2-fluorobenzyl)-1H-pyrazolo[3,4-b]-pyridin-3-yl]-5-pyrimidinyl}-2,5-diazabicyclo[2.2.1]heptane-2-carboxylate (example VI, step 4) are dissolved in 2 ml of DCM, and 2 ml of TFA are added. The mixture is stirred at RT for one hour. It is diluted with DCM, and the solution is made basic with aqueous sodium carbonate solution. The organic phase is separated off, washed with saturated aqueous sodium chloride solution and dried. The solvent is removed in vacuo to result in 163 mg (82% of theory) of the product.

LC/MS (method D): R$_t$=2.65 min.
MS (ESIpos): m/z=402.5 (M+H)$^+$
$^1$H-NMR (300 MHz, DMSO-d$_6$): δ=1.76 (dd, 2H), 2.85 (dd, 2H), 3.07 (d, 1H), 3.56 (d, 1H), 3.69 (s, 1H), 4.59 (s, 1H), 5.80 (s, 2H), 7.09–7.28 (m, 3H), 7.30–7.43 (m, 2H), 8.30 (s, 2H), 8.62 (d, 1H), 8.81 (d, 1H).

The examples listed in the following table can be prepared from the appropriate starting compounds in analogy to the method of example 9:

| Ex. No. | Structure | Analytical data |
|---|---|---|
| 10 | 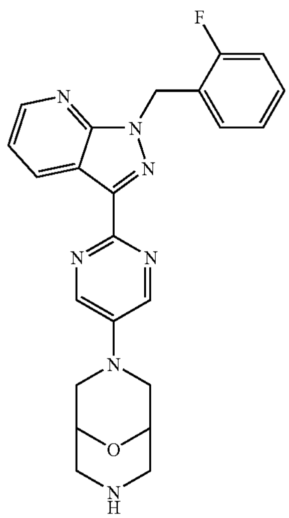 | LC/MS(method A): $R_t$=1.68 min. MS(ESIpos): m/z=432(M+H)$^+$ $^1$H-NMR(200MHz, DMSO-d$_6$): δ=3.03–3.47 (m, 7H), 3.85–4.00(m, 3H), 4.11(br s, 1H), 5.83 (s, 2H), 7.08–7.47(m, 5H), 8.61(s, 2H), 8.64 (d, 1H), 8.84(d, 1H). |
| 11 | 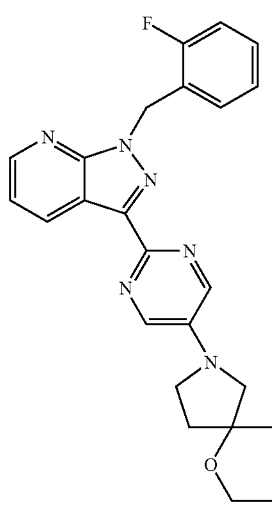 | LC/MS(method A): $R_t$=1.75 min. MS(ESIpos): m/z=456(M+H)$^+$ $^1$H-NMR(200MHz, DMSO-d$_6$): δ=2.03 (quintet, 1H), 2.15 (quintet, 1H), 2.69(t, 3H), 2.77(q, 1H), 3.38–3.65(m, 7H), 5.80(s, 2H), 7.09–7.19 (m, 3H), 7.32–7.41(m, 2H), 8.25(s, 2H), 8.62 (d, 1H), 8.83(d, 1H). |
| 12 | | LC/MS(method A): $R_t$=1.71 min. MS(ESIpos): m/z=404(M+H)$^+$ $^1$H-NMR(200MHz, DMSO-d$_6$): δ=1.77–2.26 (m, 3H), 2.32(s, 3H), 3.09–3.22(m, 1H), 3.33–3.60(m, 4H), 5.80(s, 2H), 7.06–7.45 (m, 5H), 8.24(s, 2H), 8.62(d, 1H), 8.84(d, 1H). |

EXAMPLE 13

2-{2-[1-(2-Fluorobenzyl)-1H-pyrazol[3,4-b]pyridin-3-yl]-5-pyrimidinyl}-cyclohexanone

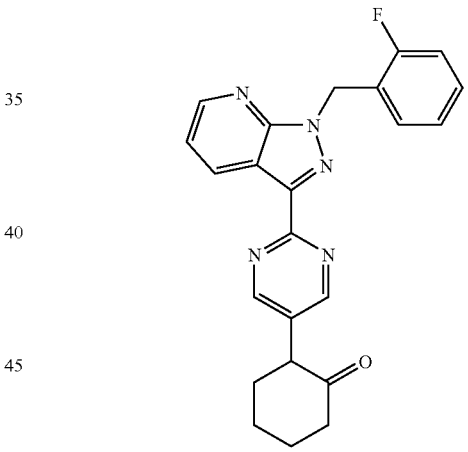

The compound is prepared in analogy to the method of example 1 apart from the following modifications. The reaction is carried out in absolute dioxane with sodium tert-butoxide instead of the corresponding potassium compound and at 70° C. Starting from 100 mg (0.26 mmol) of 3-(5-bromo-2-pyrimidinyl)-1-(2-fluorobenzyl)-1H-pyrazol [3,4-b]pyridine (example I, step 6) and 77 mg (0.78 mmol) of cyclohexanone, 31 mg (29% of theory) of the product are obtained.

LC/MS (method D): $R_t$=4.26 min.
MS (ESIpos): m/z=402.3 (M+H)$^+$
$R_f$=0.40 (toluene/ethyl acetate 1:1)
$^1$H-NMR (200 MHz, DMSO-d$_6$): δ=1.70–2.43 (m 7H), 2.54–2.72 (m, 1H), 3.99 (dd, 1H), 5.87 (s, 2H), 7.11–7.50 (m, 5H), 8.68 (d, 1H), 8.70 (s, 2H), 8.89 (d, 1H).

The example detailed in the following table can be prepared from the appropriate starting compound in analogy to the method of example 13:

| Ex. No. | Structure | Analytical data |
|---|---|---|
| 14 | 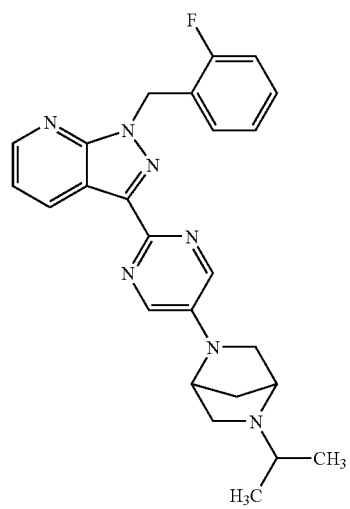 | LC/MS(method C): $R_t$= 4.73 min.<br>MS(ESIpos): m/z= 430.4(M+H)$^+$<br>$R_f$=0.56(toluene/ethyl acetate)<br>$^1$H-NMR(200MHz, DMSO-d$_6$): δ=1.06(s, 3H), 1.32(s, 3H), 1.61–1.95(m, 3H), 2.01–2.38(m, 2H), 2.62–2.89(m, 1H), 4.13(dd, 1H), 5.87(s, 2H), 7.21(q, 3H), 7.32–7.50(m, 2H), 8.68(d, 1H), 8.75(s, 2H), 8.88(d, 1H). |

EXAMPLE 15

1-(2-Fluorobenzyl)-3-[5-(5-isopropyl-2,5-diazabicyclo[2.2.1]hept-2-yl)-2-pyrimidinyl]-1H-pyrazol[3,4-b]pyridine 50 mg (0.13 mmol) of 3-[5-(2,5-diazabicyclo[2.2.1]hept-2-yl)-2-pyrimidinyl]-1-(2-fluorobenzyl)-1H-pyrazolo[3,4-b]pyridine (example 9) are dissolved in 5 ml of absolute acetone, and 92 mg (0.87 mmol) of sodium carbonate are added. 64 mg (0.37 mmol) of 2-iodopropane are added to the suspension, and the mixture is stirred at RT overnight. The reaction solution is mixed with water and extracted with DCM. The organic phases are combined, washed with saturated aqueous sodium chloride solution, dried and filtered. The solvent is removed in vacuo, and the residue is purified by preparative HPLC with addition of small portions of aqueous hydrochloric acid. 25 mg (42% of theory) of the product are obtained.

LC/MS (method A): $R_t$=1.78 min.
MS (ESIpos): m/z=444 (M+H)$^+$.

EXAMPLE 16

5-{2-[1-(2-Fluorobenzyl)-1H-pyrazolo[3,4-b]pyridin-3-yl]-5-pyrimidinyl}-2,2-dimethyl-5-aza-2-azoniabicyclo[2.2.1]heptane chloride

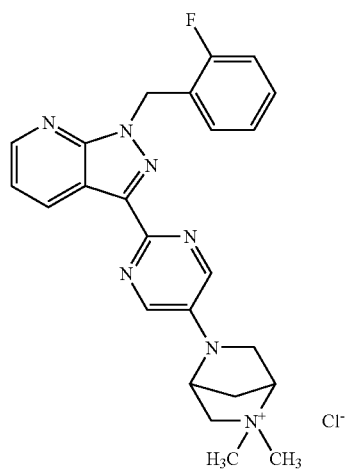

The compound is prepared in analogy to the method for example 15 using the appropriate starting materials. 51 mg (88% of theory) of the product are obtained.

LC/MS (method A): $R_t$=1.65 min.
MS (ESIpos): m/z=430 (M+H)$^+$
$^1$H-NMR (200 MHz, DMSO-d$_6$): δ=2.34 (d, 1H), 2.71 (d, 1H), 3.11 (s, 3H), 3.28 (s, 3H), 3.62–3.76 (m, 3H), 4.64 (s, 1H), 4.90 (s, 1H), 5.82 (s, 2H), 7.11–7.29 (m, 3H), 7.32–7.44 (m, 2H), 8.44 (s, 2H), 8.63 (d, 1H), 8.82 (d, 1H).

EXAMPLE 17

1-(2-Fluorobenzyl)-3-[5-(5-methyl-2,5-diazabicyclo[2.2.1]hept-2-yl)-2-pyrimidinyl-1H-pyrazolo[3,4-b]pyridine

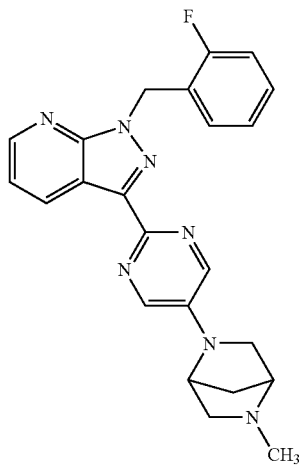

40 mg (0.10 mmol) of 3-[5-(2,5-diazabicyclo[2.2.1]hept-2-yl)-2-pyrimidinyl]-1-(2-fluorobenzyl)-1H-pyrazolo[3,4-b]pyridine (example 9) are dissolved in 0.5 ml of absolute DMF. 542 mg (6.67 mmol) of aqueous formaldehyde solution (37% strength) and 1220 mg (26.51 mmol) of formic acid are added to this solution, and the reaction mixture is heated at 80° C. for 16 hours. The reaction solution is made basic with 1 molar sodium hydroxide solution and extracted with DCM. The organic phase is washed with saturated aqueous sodium chloride solution and dried, and the solvent is removed in vacuo. 39 mg (94% of theory) of the product are obtained.

HPLC: $R_t$=3.39 min.

LC/MS (method C): $R_t$=2.61 min.

MS (ESIpos): m/z=416.24 (M+H)$^+$ $^1$H-NMR (400 MHz, DMSO-d$_6$): δ=1.78 (d, 1H), 1.93 (d, 1H), 2.28 (s, 3H), 2.73 (s, 1H), 2.81 (d, 1H), 2.89 (s, 1H), 3.32 (d, 1H), 3.38 (d, 1H), 3.51 (s, 1H), 5.81 (s, 2H), 7.10–7.28 (m, 3H), 7.32–7.43 (m, 2H), 8.32 (s, 2H), 8.62 (d, 1H), 8.81 (d, 1H).

EXAMPLE 18

2-{2-[1-(2-Fluorobenzyl)-1H-pyrazolo[3,4-b]pyridin-3-yl]-5-pyrimidinyl}-9-methyl-6-oxa-2,9-diazaspiro[4.5]decane hydrochloride

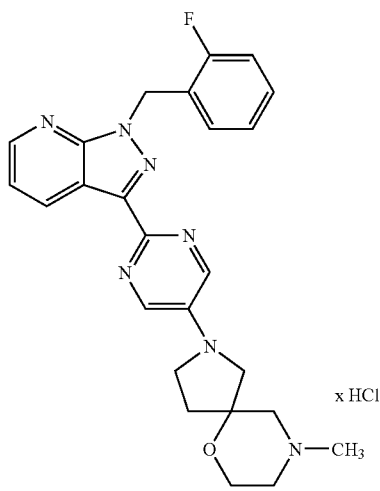

The compound is prepared from example 11 in analogy to the method for example 17. 49 mg (88% of theory) of the product are obtained. The hydrochloride is formed during the purification by HPLC with addition of small portions of hydrochloric acid.

LC/MS (method D): $R_t$=2.78 min.

MS (ESIpos): m/z=460.4 (M+H)$^+$ $^1$H-NMR (300 MHz, DMSO-d$_6$): δ=2.09–2.40 (m, 2H), 2.57–2.74 (m, 1H), 2.80 (s, 3H), 3.00–3.25 (m, 2H), 3.29–3.70 (m, 6H), 3.80–4.03 (m, 3H), 5.81 (s, 2H), 7.10–7.29 (m, 3H), 7.33–7.45 (m, 2H), 8.26 (d, 2H), 8.63 (d, 1H), 8.84 (t, 1H), 11.20 (br s, 1H).

EXAMPLE 19

1-(2-Fluorobenzyl)-3-[5-(8-oxa-3-azabicyclo[3.2.1]oct-3-yl)-2-pyrimidinyl]-1H-pyrazolo[3,4-b]pyridine

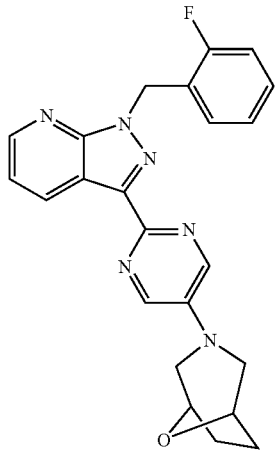

400 mg (0.68 mmol) of 3-[4,6-dichloro-5-(8-oxa-3-azabicyclo[3.2.1]oct-3-yl)-2-pyrimidinyl]-1-(2-fluorobenzyl)-1H-pyrazolo[3,4-b]pyridine (example XII, step 7) are dissolved in 200 ml of methanol, and 86 mg of ammonium formate are added. Under argon, 26 mg of palladium on activated carbon (10%) are added, and the mixture is heated under reflux for 3 days. The reaction mixture is filtered and the residues are washed with methanol. The solvent is removed in vacuo, and the residue is purified by preparative HPLC. 99 mg (35% of theory) of the product are obtained.

LC/MS (method D): $R_t$=3.97 min.

MS (ESIpos): m/z=417 (M+H)$^+$ $^1$H-NMR (200 MHz, DMSO-d$_6$): δ=1.88 (s, 4H), 2.98 (dd, 2H), 3.61 (d, 1H), 4.49 (s, 2H), 5.82 (s, 2H), 7.09-7.46 (m, 5H), 8.53 (s, 2H), 8.64 (dd, 1H), 8.82 (dd, 1H).

EXAMPLE 20

1-(2-Fluorobenzyl)-3-{5-[(3S)-3-methoxy-1-pyrrolidinyl]-2-pyrimidinyl}-1H-pyrazolo[3,4-b]pyridine

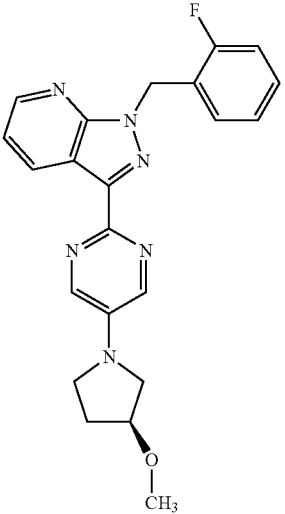

100 mg (0.21 mmol, purity 80%) of (3S)-1-{2-[1-(2-fluorobenzyl)-1H-pyrazolo[3,4-b]pyridin-3-yl]-5-pyrimidinyl}-3-pyrrolidinol (example XIX, step 3) are dissolved in 2 ml of DMF under argon and, while cooling in an ice bath 8 mg (0.33 mmol) of sodium hydride are added. 32 mg (0.23 mmol) of iodomethane are added dropwise to the suspension, likewise while cooling in an ice bath, and the mixture is stirred at this temperature for 2 hours. 0.5 ml of distilled water is added, and the reaction mixture is chromatographed directly on a preparative HPLC. 35 mg (42% of theory) of the product are obtained.

LC/MS (method D): $R_t$=4.12 min.
MS (ESIpos): m/z=405.4 (M+H)$^{30}$
$^1$H-NMR (300 MHz, DMSO-d$_6$): δ=2.05–2.18 (m, 2H), 3.29 (s, 3H), 3.34–3.57 (m, 4H), 4.14 (br s, 1H), 5.80 (s, 2H), 7.10–7.28 (m, 3H), 7.29–7.43 (m, 2H), 8.26 (s, 2H), 8.61 (d, 1H), 8.81 (d, 1H).

The examples listed in the following table can be prepared from the appropriate starting compounds in analogy to the method of example 20:

| Ex. No. | Structure | Analytical data |
|---|---|---|
| 21 | 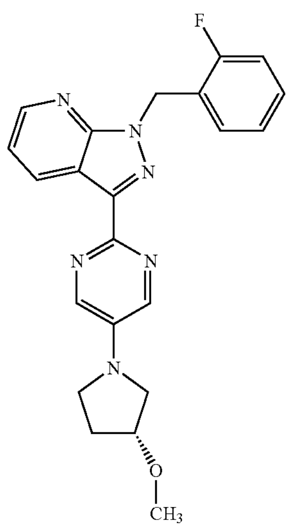 | LC/MS(method D): $R_t$=4.12 min. MS(ESIpos): m/z=405.3(M+H)$^+$ $^1$H-NMR(300MHz, DMSO-d$_6$): δ=2.03–2.19(m, 2H), 3.29(s, 3H), 3.35–3.53(m, 4H), 4.15(br s, 1H), 5.81(s, 2H), 7.10–7.26(m, 3H), 7.29–7.44(m, 2H), 8.28(d, 1H), 8.82(d, 1H). |
| 22 | 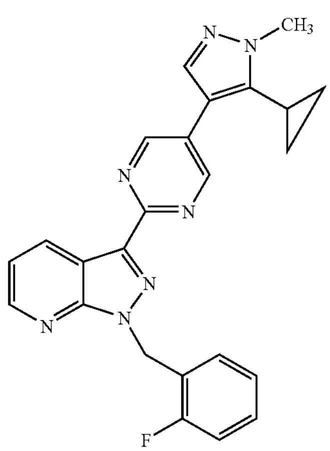 | HPLC: $R_t$=4.69 min. MS(ESIpos): m/z=426(M+H)$^+$ $R_f$=0.62(DCM/methanol 20:1) $^1$H-NMR(300MHz, DMSO-d$_6$): δ=0.45 (q, 1H), 0.82(quintet, 1H), 0.90–0.97(m, 1H), 1.06–1.14(m, 1H), 1.97–2.15(m, 1H), 3.81(s, 2H), 3.92(s, 1H), 5.87(s, 2H), 7.17(q, 1H), 7.22(q, 2H), 7.36(t, 1H), 7.44(dd, 1H), 8.18(s, 1H), 8.68(d, 1H), 8.90(d, 1H), 9.13(d, 2H). |

EXAMPLE 23

3-[5-(1,3-Benzodioxol-5-yl)-2-pyrimidinyl]-1-(2-fluorobenzyl)-1H-pyrazolo[3,4-b]-pyridine

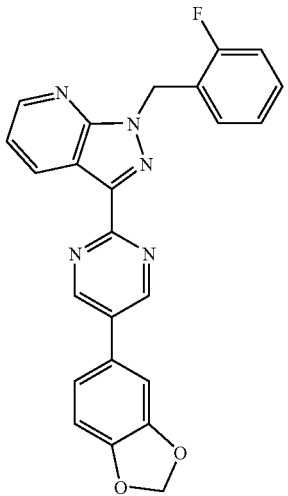

120 mg (0.31 mmol) of 3-(5-bromo-2-pyrimidinyl)-1-(2-fluorobenzyl)-1H-pyrazolo[3,4-b]pyridine (example I, step 6) are dissolved in 10 ml of DME under argon, and 67 mg (0.41 mmol) of 1,3-benzodioxol-5-yl-boronic acid are added. The mixture is heated to 40° C. until a solution is produced, and then 17 mg (0.02 mmol) of tetrakis(triphenylphosphine)palladium(0) are added. The mixture is stirred under reflux for one hour, then 39 mg (0.34 mmol) of potassium tert-butoxide are added, and the mixture is then stirred at 85° C. overnight. It is diluted with DCM and extracted once each with 1 molar hydrochloric acid and saturated aqueous sodium bicarbonate solution. The organic phase is dried over magnesium sulfate and filtered, and the solvent is removed in vacuo. The residue is purified by preparative HPLC. 60 mg (92% of theory) of the product are obtained.

LC/MS (method D): $R_t$=4.69 min.
MS (ESIpos): m/z=426.2 (M+H)$^+$
$R_f$=0.77 (toluene/ethyl acetate 1:1)

$^1$H-NMR (300 MHz, DMSO-d$_6$): δ=5.87 (s, 2H), 6.11 (s, 2H), 7.05–7.39 (m, 5H), 7.44 (q, 1H), 7.51 (d, 1H), 7.54–7.68 (m, 1H), 8.68 (d, 1H), 8.90 (d, 1H), 9.22 (s, 2H).

The examples listed in the following table can be prepared from the appropriate starting compounds in analogy to the method of example 23:

| Ex. No. | Structure | Analytical data |
|---|---|---|
| 24 | 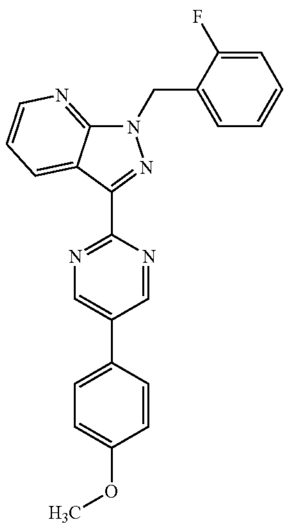 | LC/MS(method D): R<sub>t</sub>=4.77 min. MS(ESIpos): m/z=412.2(M+H)<sup>+</sup> R<sub>f</sub>=0.75(toluene/ethyl acetate 1:1) $^1$H-NMR(300MHz, DMSO-d$_6$): δ=3.98(s, 3H), 6.02(s, 2H), 7.28(t, 3H), 7.36(q, 2H), 7.51(q, 1H), 7.59(dd, 1H), 7.98(d, 2H), 8.83(d, 1H), 9.06(d, 1H), 9.38(s, 2H). |
| 25 | 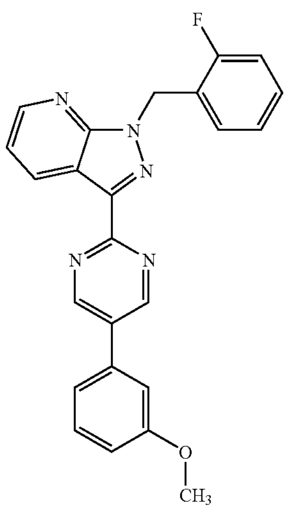 | LC/MS(method D): R$_t$=4.80 min. MS(ESIpos): m/z=412.2(M+H)$^+$ R$_f$=0.80(toluene/ethyl acetate 1:1) $^1$H-NMR(300MHz, DMSO-d$_6$): δ=3.86(s, 2H), 5.88(s, 2H), 7.05(d, 1H), 7.16(q, 1H), 7.23–7.53(m, 7H), 8.68(d, 1H), 8.91(d, 1H), 9.28(s, 2H). |
| 26 | 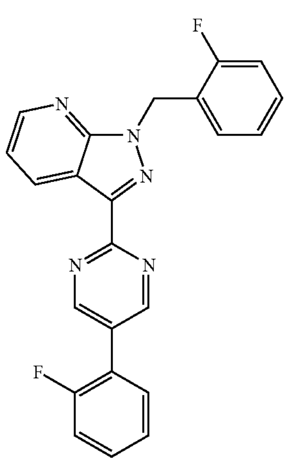 | LC/MS(method D): R$_t$=4.82 min. MS(ESIpos): m/z=400.5(M+H)$^+$ $^1$H-NMR(200MHz, DMSO-d$_6$): δ=5.90(s, 2H), 7.10–7.64(m, 8H), 7.79(t, 1H), 8.71(d, 1H), 8.93(d, 1H), 9.19(s, 2H). |
| 27 | | LC/MS(method D): R$_t$=4.86 min. MS(ESIpos): m/z=412.48(M+H)$^+$ $^1$H-NMR(300MHz, DMSO-d$_6$): δ=3.85(s, 3H), 5.89(s, 2H), 7.09–7.57(m, 9H), 8.69(d, 1H), 8.93(d, 1H), 9.10(s, 2H). |
| 28 | | LC/MS(method D): R$_t$=5.07 min. MS(ESIpos): m/z=450.22(M+H)$^+$ $^1$H-NMR(300MHz, CDCl$_3$): δ=6.00(s, 2H), 6.94–7.12(m, 3H), 7.18–7.28(m, 1H), 7.32(dd, 1H), 7.63–7.91(m, 4H), 8.64(d, 1H), 8.99(d, 1H), 9.12(s, 2H). |
| 29 | | LC/MS(method D): R$_t$=4.55 min. MS(ESIpos): m/z=407.24(M+H)$^+$ $^1$H-NMR(300MHz, DMSO-d$_6$): δ=5.90(s, 2H), 7.18(q, 1H), 7.23–7.43(m, 2H), 7.47(dd, 1H), 7.78(t, 1H), 7.96(d, 1H), 8.25(d, 1H), 8.44(s, 1H), 8.70(d, 1H), 8.92(d, 1H), 9.37(s, 2H). |

EXAMPLE 30

(2-{2-[1-(2-Fluorobenzyl)-1H-pyrazolo[3,4-b]pyridin-3-yl]-5-pyrimidinyl}phenyl)-methanol

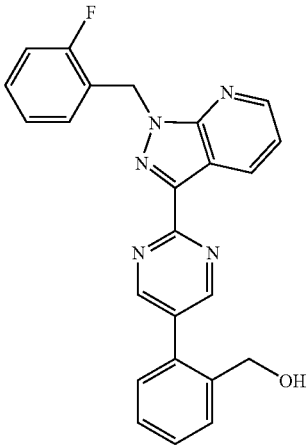

200 mg (0.52 mmol) of 3-(5-bromo-2-pyrimidinyl)-1-(2-fluorobenzyl)-1H-pyrazolo-[3,4-b]pyridine (example I, step 6), 90 mg (0.62 mmol) of 2-(hydroxymethyl)-phenylboronic acid, 40 mg (0.05 mmol) of 1,1'-bis(diphenylphosphino)-ferrocenepalladium(II) chloride and 200 mg (0.62 mmol) of cesium carbonate are taken up in 2 ml of DME and stirred under reflux overnight. The solvent is removed under vacuum, and the residue is purified by preparative HPLC to result in 111 mg (52% of theory) of the product.

HPLC: $R_t$=4.53 min.

LC/MS (method C): $R_t$=4.17 min.

MS (ESIpos): m/z=412 (M+H)$^+$ $^1$H-NMR (200 MHz, CDCl$_3$): δ=1.26 (t, 1H), 4.65 (d, 2H), 6.00 (s, 2H), 6.92–7.70 (m, 9H), 8.64 (d, 1H), 9.00 (s, 2H), 9.03 (d, 1H).

EXAMPLE 31

1-(2-Fluorobenzyl)-3-[5-(2-fluor-4-pyridinyl)-2-pyrimidinyl]-1H-pyrazolo[3,4-b]-pyridine

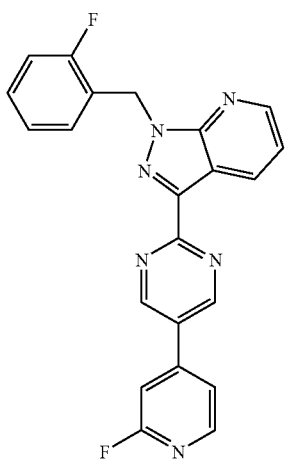

120 mg (0.31 mmol) of 3-(5-bromo-2-pyrimidinyl)-1-(2-fluorobenzyl)-1 H-pyrazolo[3,4-b]pyridine (example I, step 6) are dissolved in 10 ml of DMF under argon, and 121 mg (0.31 mmol) of 2-fluoro-4-(tributylstannyl)pyridine (example XX) and 13 mg (0.02 mmol) of dichlorobis(triphenylphosphine)palladium are added. The reaction mixture is stirred at 110° C. overnight. It is diluted with DCM and extracted with saturated aqueous ammonium chloride solution. The organic phase is dried over magnesium sulfate and filtered, and the solvent is removed in vacuo. The residue is purified by preparative HPLC. 41 mg (32% of theory) of the product are obtained.

LC/MS (method D): $R_t$=4.17 min.

MS (ESIpos): m/z=401.25 (M+H)$^+$ $R_f$=0.67 (toluene/ethyl acetate 2:1)

$^1$H-NMR (300 MHz, DMSO-d$_6$): δ=5.91 (s, 2H), 7.18 (q, 1H), 7.22–7.43 (m, 3H), 7.48 (dd, 1H), 7.91 (t, 1H), 8.63 (d, 1H), 8.71 (d, 1H), 8.80 (d, 1H), 8.93 (d, 1H), 9.30 (s, 2H).

The examples listed in the following table can be prepared from the appropriate starting compounds in analogy to the method of example 31:

| Ex. No. | Structure | Analytical data |
|---|---|---|
| 32 | 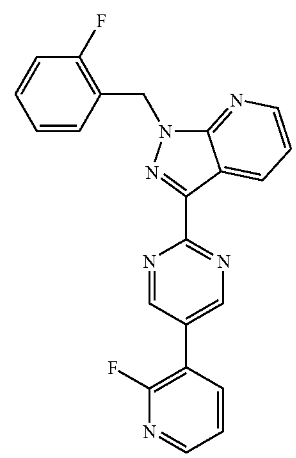 | LC/MS(method C): $R_t$=4.31 min. MS(ESIpos): m/z=401.5(M+H)$^+$ $R_f$=0.27(toluene/ethyl acetate 2:1) $^1$H-NMR(200MHz, DMSO-d$_6$): δ=5.91(s, 2H), 7.11–7.42(m, 4H), 7.48(dd, 1H), 7.59(t, 1H), 8.34–8.48(m, 2H), 8.72(d, 1H), 8.92(d, 1H), 9.25(s, 2H). |
| 33 | 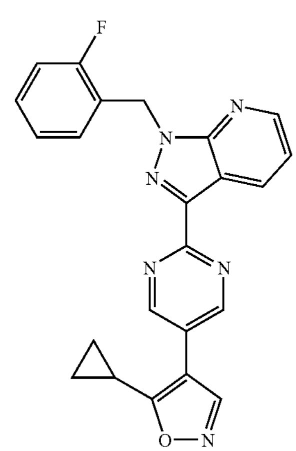 | HPLC: $R_t$=4.90 min. MS(ESIpos): m/z=413.1(M+H)$^+$ $R_f$=0.33(DCM/methanol 20:1) $^1$H-NMR(400MHz, DMSO-d$_6$): δ= 1.03–1.11(m, 2H), 1.18–1.29(m, 2H), 2.45–2.54(m, 1H), 5.89(s, 2H), 7.16(t, 1H), 7.22–7.30(m, 2H), 7.35–7.41(m, 1H), 7.46(dd, 1H), 8.70(d, 1H), 8.91(d, 1H), 9.09(s, 1H), 9.23(s, 2H). |

-continued

| Ex. No. | Structure | Analytical data |
|---|---|---|
| 34 | 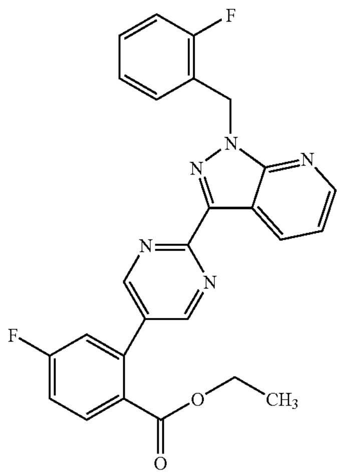 | HPLC: R$_t$=5.18 min. MS(ESIpos): m/z=472(M+H)$^+$ R$_f$=0.66(DCM/ethyl acetate 1:1) $^1$H-NMR(300MHz, DMSO-d$_6$): δ= 1.08(t, 3H), 4.13(q, 2H), 5.90(s, 2H), 7.11–7.60(m, 7H), 8.11(dd, 1H), 8.70(d, 1H), 8.81(d, 3H). |
| 35 | 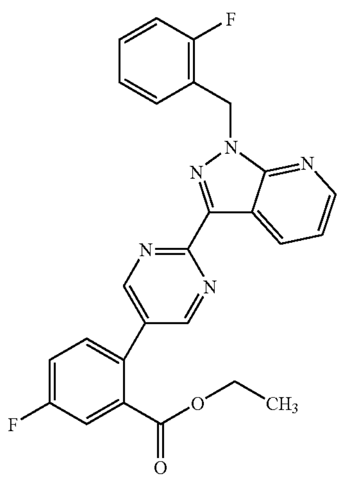 | HPLC: R$_t$=5.16 min. MS(ESIpos): m/z=472(M+H)$^+$ R$_f$=0.66(DCM/ethyl acetate 1:1) $^1$H-NMR(200MHz, DMSO-d$_6$): δ= 1.09(t, 3H), 4.16(q, 2H), 5.90(s, 2H), 7.11–7.51(m, 5H), 7.44(dd, 1H), 7.68(d, 1H), 7.82(d, 1H), 8.70(d, 1H), 8.92(d, 3H). |

EXAMPLE 36

3-[5-(5-Cyclopropyl-1H-pyrazol-4-yl)-2-pyrimidinyl]-1-(2-fluorobenzyl)-1 H-pyrazolo[3,4-b]pyridine

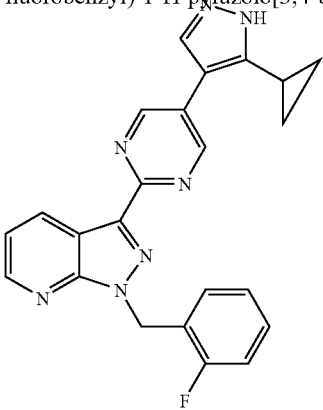

90 mg (0.20 mmol) of (2E)-1-cyclopropyl-3-(dimethylamino)-2-{2-[1-(2-fluorobenzyl)-1H-pyrazolo[3,4-b]pyridin-3-yl]-5-pyrimidinyl}-2-propen-1-one (example XXVI, step 2) are dissolved in 3 ml of absolute methanol under argon. 102 mg (2.03 mmol) of hydrazine hydrate are added, and the mixture is stirred under reflux for 2 hours. The solvent is removed in vacuo, and the residue is purified by preparative HPLC. 48 mg (58% of theory) of the product are obtained.

HPLC: R$_t$=4.37 min.
MS (ESIpos): m/z=412 (M+H)$^+$
R$_f$=0.36 (DCM/methanol 20:1).

EXAMPLE 37

3-{5-[5-Cyclopropyl-1-(2,2,2-trifluoroethyl)-1H-pyrazol-4-yl]-2-pyrimidinyl}-1-(2-fluorobenzyl)-1H-pyrazolo[3,4-b]pyridine

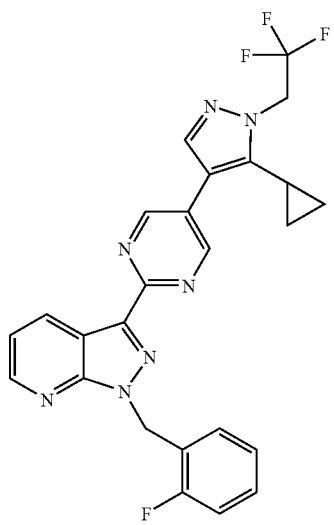

The compound is prepared in analogy to the method for example 36 using 2,2,2-trifluoroethylhydrazine. The yield of the product is 9% of theory.

LC/MS (method A): R$_t$=2.87 min.
MS (ESIpos): m/z=494 (M+H)$^+$
R$_f$=0.70 (DCM/methanol 20:1).

EXAMPLE 38

1-{2-[1-(2-Fluorobenzyl)-1H-pyrazol[3,4-b]pyridin-3-yl]-5-pyrimidinyl}-3-pyrrolidinone

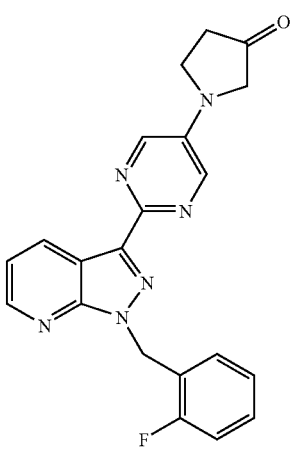

100 mg (0.26 mmol) of (3R)-1-{2-[1-(2-fluorobenzyl)-1H-pyrazolo[3,4-b]pyridin-3-yl]-5-pyrimidinyl}-3-pyrrolidinol (example XIX, step 3) are introduced into a freshly prepared solution of 0.11 ml of triethylamine and 33 µl of DMSO under argon, and the resulting solution is cooled to 0° C. 73 mg (0.46 mmol) of sulfur trioxide-pyridine complex are added, and the mixture is stirred at 0° C. for one hour. It is then allowed to warm to RT and is stirred at this temperature overnight. The reaction solution is mixed with 100 ml of distilled water and extracted three times with DCM. The organic phase is washed once each with 1 mol of hydrochloric acid and distilled water, and the solvent is removed under vacuum. The residue is purified by preparative HPLC. 5 mg (5% of theory) of the product are obtained.

LC/MS (method C): $R_t$=3.85 min.

MS (ESIpos): m/z=389.4 (M+H)$^+$ $R_f$=0.36 (DCM/ethyl acetate 2:1)

$^1$H-NMR (200 MHz, DMSO-d$_6$): δ=2.74 (t, 2H), 3.77 (t, 2H), 3.80 (s, 2H), 5.82 (s, 2H), 7.10–7.48 (m, 5H), 8.42 (s, 2H), 8.64 (d, 1H), 8.84 (d, 1H).

EXAMPLE 39

1-(2-Fluorobenzyl)-3-[5-(2-methoxy-4-pyridinyl)-2-pyrimidinyl]-1H-pyrazolo-[3,4-b]pyridine

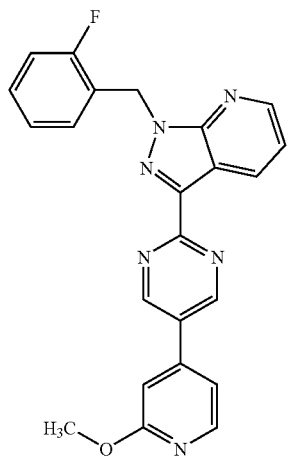

30 mg (0.08 mmol) of 1-(2-fluorobenzyl)-3-[5-(2-fluoro-4-pyridinyl)-2-pyrimidinyl]-1H-pyrazolo[3,4-b]pyridine (example 31) are dissolved in 3 ml of methanol, and 32 mg (0.60 mmol) of sodium methanolate are added. The solution is stirred under reflux for 3 days. The solution is diluted with DCM and extracted twice with distilled water and once with saturated aqueous sodium chloride solution. The organic phase is dried over magnesium sulfate and filtered, and the solvent is removed in vacuo. 34 mg of the product are obtained.

LC/MS (method C): $R_t$=3.64 min.

MS (ESIpos): m/z=413.4 (M+H)$^+$ $R_f$=0.80 (DCM/methanol 20:1)

$^1$H-NMR (400 MHz, DMSO-d$_6$): δ=3.99 (s, 3H), 5.90 (s, 2H), 7.17 (t, 1H), 7.22–7.33 (m, 2H), 7.47 (dd, 1H), 7.63 (d, 1H), 8.38 (d, 1H), 8.58 (s, 1H), 8.71 (d, 1H), 8.93 (d, 1H), 9.21 (s, 2H).

The invention claimed is:

1. A compound of the formula

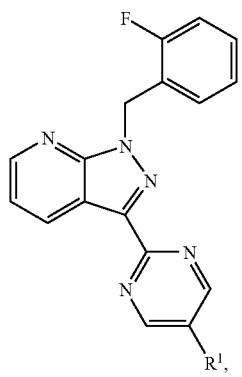

(I)

in which

R$^1$ is C$_6$–C$_{10}$-aryl or 5- to 10-membered heteroaryl which are optionally substituted by radicals selected from the group of halogen, cyano, C$_1$–C$_6$-alkoxy, C$_1$–C$_6$-alkoxycarbonyl, trifluoromethyl, 2,2,2-trifluoroethyl, trifluoromethoxy, C$_1$–C$_4$-alkyl and C$_3$–C$_8$-cycloalkyl, where C$_1$–C$_4$-alkyl is optionally substituted by hydroxy, or a group of the formula

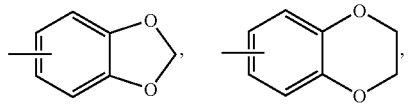

or 4- to 12-membered heterocyclyl which is bonded via a nitrogen atom and which is optionally substituted by radicals selected from the group of —NHR$^2$, halogen, C$_1$–C$_6$-alkoxycarbonyl, C$_1$–C$_6$-alkoxy, C$_1$–C$_6$-alkyl and oxo, where C$_1$–C$_6$-alkyl is optionally substituted by hydroxy, and R$^2$ is C$_1$–C$_4$-alkyl, or C$_4$–C$_8$-cycloalkyl which is substituted in the position adjacent to the point of attachment by oxo, and which is optionally substituted by C$_1$–C$_4$-alkyl, or a salt thereof.

2. The compound as claimed in claim 1, where

R$^1$ is phenyl or 5- to 6-membered heteroaryl, which are optionally substituted by radicals selected from the group of fluorine, chlorine, cyano, C$_1$–C$_3$-alkoxycarbonyl, C$_1$–C$_3$-alkoxy, trifluoromethyl, 2,2,2-trifluoroethyl, trifluoromethoxy, C$_1$–C$_3$-alkyl and C$_3$–C$_8$-cycloalkyl, where C$_1$–C$_3$-alkyl is optionally substituted by hydroxy, or a group of the formula

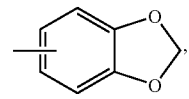

or
- 4- to 12-membered heterocyclyl which is bonded via a nitrogen atom and which is optionally substituted by radicals selected from the group of —NHR², fluorine, chlorine, $C_1$–$C_3$-alkyl, $C_1$–$C_3$-alkoxycarbonyl, $C_1$–$C_3$-alkoxy and oxo, where $C_1$–$C_3$-alkyl is optionally substituted by hydroxy, and
- R² is $C_1$–$C_3$-alkyl, or
- cyclohexyl which is substituted in the position adjacent to the point of attachment by oxo, and which is optionally substituted by $C_1$–$C_2$-alkyl,
- or a salt thereof.

3. The compound as claimed in claim 1 or 2, where
- R¹ is phenyl or pyridyl, pyrazolyl, isoxazolyl, which are optionally substituted by radicals selected from the group of fluorine, chlorine, cyano, methoxy, methoxycarbonyl, ethoxycarbonyl, trifluoromethyl, 2,2,2-trifluoroethyl, trifluoromethoxy, methyl, cyclopropyl or hydroxymethyl,
- or a group of the formula

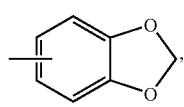

or
- 4- to 12-membered heterocyclyl which is bonded via a nitrogen atom and which is optionally substituted by radicals selected from the group of —NHR², fluorine, chlorine, $C_1$–$C_3$-alkyl, methoxy, ethoxy, hydroxymethyl and oxo, and
- R² is methyl, or
- cyclohexyl which is substituted in the position adjacent to the point of attachment by oxo, and which is optionally substituted by methyl,
- or a salt thereof.

4. A process for preparing compounds of the formula (IV), (VI) and (VII), characterized in that either
[A] compounds of the formula

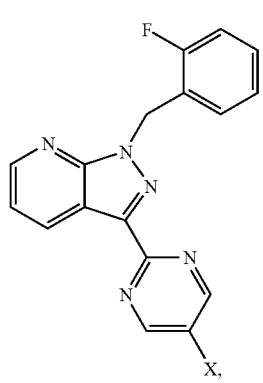

in which X is chlorine, bromine, iodine,
are reacted with a compound of the formula

R³—NH—R⁴ in which
- R³, R⁴ together with the nitrogen atom to which they are bonded are a 4- to 12-membered heterocyclyl which is optionally substituted by radicals selected from the group of —NHR², halogen, $C_1$–$C_6$-alkoxycarbonyl, $C_1$–$C_6$-alkoxy, $C_1$–$C_6$-alkyl and oxo, where $C_1$–$C_6$-alkyl is optionally substituted by —OR⁵, and R² has the meaning indicated in claim 1, R⁵ is a hydroxy protective group in an inert solvent in the presence of a base and of a transition metal catalyst to give compounds of the formula

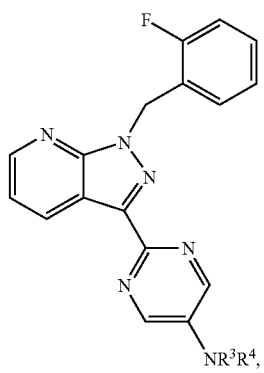

or
[B] compounds of the formula (II) are reacted with a compound of the formula

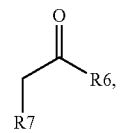

in which
- R⁶ is cycloalkyl, R⁷ is hydrogen or R⁶ and R⁷ together with the CH₂CO group to which they are bonded are cycloalkyl which may be substituted by $C_1$–$C_6$-alkyl radicals, in an inert solvent in the presence of a base and of a transition metal catalyst to give compounds of the formula

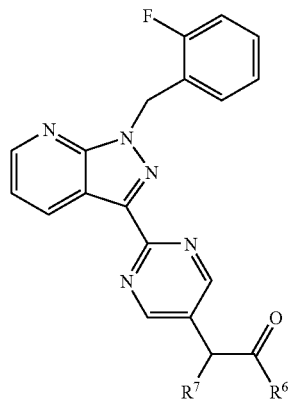

or

[C] compounds of the formula (II) are reacted with a compound of the formula $$A-R^8 \quad (VII),$$

in which

A is $-B(OR^9)_2$ or $-Sn(C_1-C_6\text{-alkyl})_3$, where $R^9$ is hydrogen, $C_1-C_6$-alkyl or two radicals together form a $-CH_2CH_2-$ or $-(CH_3)_2C-C(CH_3)_2-$ bridge, and $R^8$ is $C_6-C_{10}$-aryl or 5- to 10-membered heteroaryl which are optionally substituted by radicals selected from the group of halogen, cyano, $C_1-C_6$-alkoxy, $C_1-C_6$-alkoxycarbonyl, trifluoromethyl, 2,2,2-trifluoroethyl, trifluoromethoxy, $C_1-C_4$-alkyl and $C_3-C_8$-cycloalkyl, where $C_1-C_4$-alkyl is optionally substituted by hydroxy, or a group of the formula

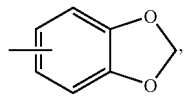 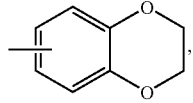

in an inert solvent in the presence of a base and of a transition metal catalyst to give compounds of the formula

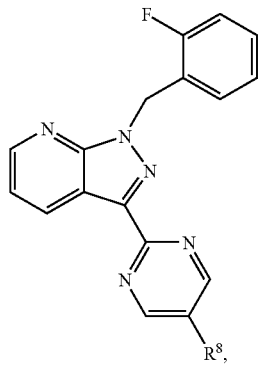

(VIII)

and the resulting compounds of the formula (IV), (VI) and (VIII) are optionally reacted with the appropriate (i) solvents and/or (ii) bases or acids to give the, salt thereof.

5. The process of claim 4, wherein X is bromine.

6. A medicament comprising at least one of the compounds as claimed in claim 1 mixed together with at least one pharmaceutically acceptable, essentially nontoxic carrier or excipient.

7. A method for the treatment of disorders of learning and/or memory comprising administering to a human or animal an effective amount of a compound of claim 1.

8. A method for the treatment of disorders of learning and/or memory diseases comprising administering to a human or animal an effective amount of a medicament of claim 6.

* * * * *